US011732009B2

(12) United States Patent
Bhatia et al.

(10) Patent No.: US 11,732,009 B2
(45) Date of Patent: Aug. 22, 2023

(54) ACTIVITY SENSOR WITH TUNABLE ANALYTE

(71) Applicant: GLYMPSE BIO, INC., Cambridge, MA (US)

(72) Inventors: Sangeeta Bhatia, Lexington, MA (US); Gabriel Kwong, Atlanta, GA (US); Eric Huang, Lexington, MA (US); Sirshendu Roopom Banerjee, Lexington, MA (US); Andrew Warren, Cambridge, MA (US); Sophie Cazanave, Cambridge, MA (US)

(73) Assignee: GLYMPSE BIO, INC., Cambridge, MA (US)

( * ) Notice: Subject to any disclaimer, the term of this patent is extended or adjusted under 35 U.S.C. 154(b) by 0 days.

(21) Appl. No.: 16/355,178

(22) Filed: Mar. 15, 2019

(65) Prior Publication Data

US 2019/0376113 A1 Dec. 12, 2019

Related U.S. Application Data

(60) Provisional application No. 62/682,492, filed on Jun. 8, 2018.

(51) Int. Cl.
*A61K 47/65* (2017.01)
*C12Q 1/37* (2006.01)
(Continued)

(52) U.S. Cl.
CPC ............. *C07K 14/00* (2013.01); *A61K 47/10* (2013.01); *A61K 47/60* (2017.08); *A61K 47/65* (2017.08);
(Continued)

(58) Field of Classification Search
CPC ........... C12Q 1/37; G01N 2333/96494; G01N 2800/085; G01N 33/54393; A61K 47/60; A61K 47/65; A61K 38/00
See application file for complete search history.

(56) References Cited

U.S. PATENT DOCUMENTS 6,592,847 B1 7/2003 Weissleder et al.
7,179,655 B2 2/2007 Patricelli
(Continued)

FOREIGN PATENT DOCUMENTS

WO 0214867 A2 2/2002
WO 2004005348 A1 1/2004
(Continued)

OTHER PUBLICATIONS

Dudani, J.S. et al., Sustained-Release Synthetic Biomarkers for Monitoring Thrombosis and Inflammation Using Point-of-Care Compatible Readouts, 2016, Advanced Functional Materials, 26, 2919-2928 (Year: 2016).*
(Continued)

*Primary Examiner* — Louise W Humphrey
*Assistant Examiner* — Anjali Ajit Hirani
(74) *Attorney, Agent, or Firm* — Wilson Sonsini Goodrich & Rosati

(57) ABSTRACT

A nanoparticle activity sensor containing a reporter and at least one tuning domain that modifies a distribution or residence time of the activity sensor when administered to a patient. When administered to the patient, the activity sensor enters cells or tissue where it is cleaved by enzymes specific to a physiological state such as a disease to release a detectable analyte. The tuning domains include molecular structures that modulate distribution or decay by protecting the particle from premature cleavage and indiscriminate hydrolysis, shielding the particle from immune detection and clearance, or by targeting the particle to specific tissue, bodily fluids, or cell types.

12 Claims, 17 Drawing Sheets
Specification includes a Sequence Listing.

(51) Int. Cl.
A61K 47/60 (2017.01)
A61K 38/00 (2006.01)
C07K 14/00 (2006.01)
G01N 33/68 (2006.01)
A61K 47/10 (2017.01)
C07K 11/02 (2006.01)

(52) U.S. Cl.
CPC ............... C07K 11/02 (2013.01); C12Q 1/37 (2013.01); G01N 33/68 (2013.01); A61K 38/00 (2013.01); G01N 2333/96494 (2013.01); G01N 2800/085 (2013.01)

(56) References Cited

U.S. PATENT DOCUMENTS

| | | | |
|---|---|---|---|
| 7,329,506 | B2 | 2/2008 | Ward et al. |
| 7,833,728 | B2 | 11/2010 | Pastorek et al. |
| 8,551,727 | B2 | 10/2013 | Kwon et al. |
| 8,673,267 | B2 | 3/2014 | Bhatia et al. |
| 9,006,415 | B2 * | 4/2015 | Ren ................... A61K 49/0008 536/24.5 |
| 10,006,916 | B2 | 6/2018 | Kwong et al. |
| 2004/0091943 | A1 | 5/2004 | Schneider |
| 2010/0131432 | A1 | 5/2010 | Kennedy et al. |
| 2010/0240050 | A1 | 9/2010 | Bhatia et al. |
| 2013/0017223 | A1 | 1/2013 | Hope et al. |
| 2013/0116405 | A1 | 5/2013 | Yu et al. |
| 2015/0018517 | A1 | 1/2015 | Rajopadhye et al. |
| 2015/0065420 | A1 | 3/2015 | Soliman et al. |
| 2015/0132230 | A1 | 5/2015 | Bossmann et al. |
| 2016/0206726 | A1 | 7/2016 | Cobbold et al. |
| 2017/0049904 | A1 | 2/2017 | Lin et al. |
| 2017/0176458 | A1 | 6/2017 | Veidal et al. |
| 2017/0369843 | A1 | 12/2017 | Kahvejian et al. |
| 2018/0023114 | A1 | 1/2018 | Morin et al. |
| 2018/0085466 | A1 | 3/2018 | Bradley et al. |
| 2018/0335429 | A1 | 11/2018 | Bhatia et al. |

FOREIGN PATENT DOCUMENTS

| | | | | |
|---|---|---|---|---|
| WO | 2008127019 | A1 | 10/2008 | |
| WO | 2010/101628 | A2 | 9/2010 | |
| WO | 2012125808 | A1 | 9/2012 | |
| WO | 2014/079802 | A2 | 5/2014 | |
| WO | 2014/197816 | A1 | 12/2014 | |
| WO | 2014197840 | A1 | 12/2014 | |
| WO | WO-2014197840 | A1 * | 12/2014 | ....... G01N 33/54306 |
| WO | 2017/180587 | A2 | 10/2017 | |
| WO | 2017177115 | A1 | 10/2017 | |
| WO | 2017/193070 | A1 | 11/2017 | |
| WO | 2018/068135 | A1 | 4/2018 | |

OTHER PUBLICATIONS

Van Lehn, R. C. et al., Penetration of lipid bilayers by nanoparticles with environmentally-responsive surfaces: simulations and theory, 2011, Soft Matter, 7, 11392-11404 (Year: 2011).*
Dudani, U.S. et al., Sustained-Release Synthetic Biomarkers for Monitoring Thrombosis and Inflammation Using Point-of-Care Compatible Readouts, 2016, Advanced Functional Materials, 26, 2919-2928 (Year: 2016).*
Lin, C. et al., PEG Hydrogels for the Controlled Release of Biomolecules in Regenerative Medicine, 2009, Pharmaceutical Research, 26(3), 631-643 (Year: 2009).*
Kwon, E.J. et al., Ultrasensitive tumor-penetrating nanosensors of protease activity, 2017, Nature Biomedical Engineering, 1(54), 1-10 (Year: 2017).*
Harris, T. J. et al., Protease-Triggered Unveiling of Bioactive Nanoparticles, 2008, Small, 4(9), 1307-1312 (Year: 2008).*
Aungier, 2016, The extracellular matrix: a new dimension in disease diagnosis and treatment, Biochem Soc 10-15.
Bonnans, 2014, Remodelling the extracellular matrix in development and disease, Nat Rev Mol cell Biol 15 (12):786-801.
Dudani, 2015, Photoactivated spatiotemporally responsive nanosensors of in vivo protease activity, ACS Nano 9(12):11708-11717.
Dudani, 2018, Harnessing protease activity to improve cancer care, Ann Rev Cell Biol 2:353-76.
Friedman, 2013, The smart targeting of nanoparticles, Curr Pharm Des 19(35):6315-6329.
Gootenberg, 2018, Multiplexed and portable nucleic acid detection platform with Cas13, Cas12a, and Csm6, Science 360(6387):439-444.
Sural, 2018, Engineered livers for infectious diseases, CMGH 5(2):131-143.
Hughes, 2017, Dissecting the role of the extracellular matrix in heart disease, Vet Sci 4(24):1-28.
Kappelhoff, 2017, Overview of transcriptomic analysis of all human proteases, non-proteolytic homologs and inhibitors, BBA Mol Cell Res 1864:2210-2219.
Kircher, 2004, A dual fluorochrome probe for imaging proteases, Bioconjugate Chem 15:242-248.
Klingler, 2012, Profiling protease activities with dynamic proteomics workflows, Proteomics 12(4-5):587-596.
Kutlu, 2018, Molecular pathogenesis of nonalcoholic steatohepatitis (NASH) related hepatocellular carcinoma, Can J Gast Hepat 2018:8543763.
Kwon, 2017, Ultrasensitive tumor-penetrating nanosensors of protease activity, Nat Biomed Eng 1: art0054.
Kwong, 2013, Mass-encoded synthetic biomarkers for multiplexed urinary monitorying of disease, Nat Biotech 31(1):63-70.
Lee, 2018, Implementation of a multiplex and quantitative proteomics platform for assessin protein lysates using DNA-barcoded antibodies, Mol Cell Proteomics 17(6):1245-1258.
Lin, 2013, Nanoparticles that sense thrombin activity as synthetic urinary biomarkers of thrombosis, ACS nano 7(10):9001-9009.
Mallinckrodt, 2003, Assessing and interpreting treatment effects in longitudinal clinical trials with missing data, Biol Psychiatry 53:754-760.
Raagel, 2010, Peptide-mediate protein delivery—which pathways are penetrable?, Biochim et Biophys Acata 1798:2240-2248.
Tascilar, 1999, Role of tumor markers and mutations in cells and pancreatic juice in the diagnosis of pancreatic cancer, Ann One 10(Suppl 4):s107-s110.
Tockman, 1992, Consideratoins in bringing a cancer biomarker to clinical application, Canc Res 52:2711s-2718s.
Dudani, 2016, Sustained-release synthetic biomarkers for monitoring thrombosis and inflammation using point-of-care compatible readouts, Adv Funct Mat 10.1002:1-10.
Kwong, 2015, Mathemetical framework for activity-based cancer biomarkers, PNAS 112(41):12627-12632.
Schuerle, 2016, Magnetically actuated protease sensors for in vivo tumor profiling, Nano Lett 16:6303-6310.
Warren, 2014, Disease detection by ultrasensitive quantification of microdosed synthetic urinary biomarkers, JACS 136:13709-13714.
Warren, 2014, Point-of-care diagnostics for noncommunicable diseases using synthetic urinary biomarkers and paper microfluidics, PNAS 111(10):3671-3676.
Abudayyeh, 2012, Nanoparticle-chaperoned urinary "synthetic biomarkers" for profiling proteases in cancer, MIT Thesis.
Deshpande, 2013, Current trends in the use of liposomes for tumor targeting, Nanomed 8(9):1509-28.
Dudani, 2018, Classification of prostate cancer using a protease activity nanosensor library, PNAS 115(36):8954-8959.
Gang, 2018, Cyclic Peptides: Promising Scaffolds for Biopharmaceuticals, Genes 9:557.
Gootenberg, 2017, Nucleic acid detection with CRISPR-Cas13a/C2c2, Science 356(6336):438-442.
Gural, 2018, Engineered livers for infection diseases, Cell Mol Gastroent Hepat 5(2):131-144.
Holt, 2018, Nanosensors to cetect protease activity in vivo for noninvasive diagnostics, J Vis Exp 137:e57937.

(56) References Cited

OTHER PUBLICATIONS

International Search Report and Written Opinion dated Oct. 24, 2019, for PCT/US2019/036039, filed Jun. 7, 2019 (11 pages).
International Search Report and Written Opinion dated Sep. 4, 2019, for PCT/US19/36155, filed Jun. 7, 2019 (8 pages).
International Search Report and Written Opinion dated Sep. 12, 2019, for PCT/US2019/036036, filed Jun. 7, 2019 (9 pages).
International Search Report and Written Opinion dated Sep. 12, 2019, for PCT/US2019/036036, filed Jun. 8, 2018 (9 pages).
International Search Report and Written Opinion dated Sep. 19, 2019, for PCT/US2019/036041, filed Jun. 7, 2019 (8 pages).
Kristensen, 2016, Cell-penetrating peptides as tools to enhance non-injectable delivery of biopharmaceuticals, Tissue Barriers 4(2):e1178369.
Kwong, 2013, Mass-encoded synthetic biomarkers for multiplexed urinary monitoring of disease, Nat Biotech 31(1):63-70.
Lau, 2018, Therapeutic peptides: Historical perspectives, current development trends, and future directions, Bioorganic & Med Chem 26:2700-2707.
Lin, 2013, The biodegradation of biodegradable polymeric biomaterials, Chapter II.4.3 in Biomaterials Science 3d Ed., Ratner et al., Eds Academic Press 716-728.
Lo, 2018, iRGD-guided tumor-penetrating nanocomplexes for therapeutic siRNA delivery to pancreatic cancer, Mol Cancer Ther 17(11):2377-2388.
Luther, 2018, Hepatic connexin 32 associates with nonalcoholic fatty liver disease severity, Hepatol Comm 2(7):786-797.
Milletti, 2012, Cell-penetrating peptides: classes, origin, and current landscape, Drug Disc Today 17:850-860.
Nguyen, 2011, The prototype HIV-1 maturation inhibitor, bevirimat, binds to the CA-SP1 cleavage site in immature Gag particles, Retrovirology 8:101 (13 pages).
Song, 2012, Prosper: An integrated feature-based tool for predicting protease substrate cleavage sites, PLoSOne 7(11):e50300 (23 pages).

* cited by examiner

SEQUENCE LISTING

<160> NUMBER OF SEQ ID NOS: 75

<210> SEQ ID NO 1
<211> LENGTH: 8
<212> TYPE: PRT
<213> ORGANISM: Homo sapiens

<400> SEQUENCE: 1

Ser Ser Thr Ser Ser Trp Tyr Ser

```
<210> SEQ ID NO 2
<211> LENGTH: 8
<212> TYPE: PRT
<213> ORGANISM: Homo sapiens

<400> SEQUENCE: 2

Pro Cys Ile Gln Ala Glu Ser Glu
1               5

<210> SEQ ID NO 3
<211> LENGTH: 8
<212> TYPE: PRT
<213> ORGANISM: Homo sapiens

<400> SEQUENCE: 3

Asp Asp Glu Glu Ile Glu Leu Ala
1               5

<210> SEQ ID NO 4
<211> LENGTH: 8
<212> TYPE: PRT
<213> ORGANISM: Homo sapiens

<400> SEQUENCE: 4

Val Leu Glu Gln Val Val Thr Ser
1               5

<210> SEQ ID NO 5
<211> LENGTH: 8
<212> TYPE: PRT
<213> ORGANISM: Homo sapiens

<400> SEQUENCE: 5

Gln Val Val Gln Val Val Leu Asp
1               5

<210> SEQ ID NO 6
<211> LENGTH: 8
<212> TYPE: PRT
<213> ORGANISM: Homo sapiens

<400> SEQUENCE: 6

Lys Ser Ile Gln Glu Ile Gln Glu
1               5

<210> SEQ ID NO 7
<211> LENGTH: 8
<212> TYPE: PRT
<213> ORGANISM: Homo sapiens

<400> SEQUENCE: 7

Lys Asp Phe Ala Ala Glu Val Val
1               5

<210> SEQ ID NO 8
<211> LENGTH: 8
<212> TYPE: PRT
<213> ORGANISM: Homo sapiens

<400> SEQUENCE: 8

Thr Ser Tyr Ala Gly Tyr Ile Glu
1               5
```

```
<210> SEQ ID NO 9
<211> LENGTH: 8
<212> TYPE: PRT
<213> ORGANISM: Homo sapiens

<400> SEQUENCE: 9

Leu Lys Val Ala Gly Gln Asp Gly
1               5

<210> SEQ ID NO 10
<211> LENGTH: 8
<212> TYPE: PRT
<213> ORGANISM: Homo sapiens

<400> SEQUENCE: 10

Phe Cys Leu His Gly Gly Leu Ser
1               5

<210> SEQ ID NO 11
<211> LENGTH: 8
<212> TYPE: PRT
<213> ORGANISM: Homo sapiens

<400> SEQUENCE: 11

Trp Met Asp Phe Gly Arg Arg Ser
1               5

<210> SEQ ID NO 12
<211> LENGTH: 8
<212> TYPE: PRT
<213> ORGANISM: Homo sapiens

<400> SEQUENCE: 12

Ser Ala Thr Ala Ala Val Asn Pro
1               5

<210> SEQ ID NO 13
<211> LENGTH: 8
<212> TYPE: PRT
<213> ORGANISM: Homo sapiens

<400> SEQUENCE: 13

Arg Glu Leu Gly Leu Gly Arg His
1               5

<210> SEQ ID NO 14
<211> LENGTH: 8
<212> TYPE: PRT
<213> ORGANISM: Homo sapiens

<400> SEQUENCE: 14

Asp Glu Gly Asp Ser Leu Asp Gly
1               5

<210> SEQ ID NO 15
<211> LENGTH: 8
<212> TYPE: PRT
<213> ORGANISM: Homo sapiens

<400> SEQUENCE: 15

Asp Glu Thr Asp Met Ala Lys Leu
1               5

<210> SEQ ID NO 16
```

```
<211> LENGTH: 8
<212> TYPE: PRT
<213> ORGANISM: Homo sapiens

<400> SEQUENCE: 16

Glu Glu Cys Asp Ala Ala Glu Gly
1               5

<210> SEQ ID NO 17
<211> LENGTH: 8
<212> TYPE: PRT
<213> ORGANISM: Homo sapiens

<400> SEQUENCE: 17

Ala Glu Val Asp Gly Asp Asp Asp
1               5

<210> SEQ ID NO 18
<211> LENGTH: 8
<212> TYPE: PRT
<213> ORGANISM: Homo sapiens

<400> SEQUENCE: 18

Asp Arg His Asp Gly Thr Ser Asn
1               5

<210> SEQ ID NO 19
<211> LENGTH: 8
<212> TYPE: PRT
<213> ORGANISM: Homo sapiens

<400> SEQUENCE: 19

Val Glu Val Asp Ala Pro Lys Ser
1               5

<210> SEQ ID NO 20
<211> LENGTH: 8
<212> TYPE: PRT
<213> ORGANISM: Homo sapiens

<400> SEQUENCE: 20

Asp Gln Thr Asp Gly Leu Gly Leu
1               5

<210> SEQ ID NO 21
<211> LENGTH: 8
<212> TYPE: PRT
<213> ORGANISM: Homo sapiens

<400> SEQUENCE: 21

Asp Ser Ile Asp Ser Phe Glu Thr
1               5

<210> SEQ ID NO 22
<211> LENGTH: 8
<212> TYPE: PRT
<213> ORGANISM: Homo sapiens

<400> SEQUENCE: 22

Asp Asp Val Asp Thr Lys Lys Gln
1               5

<210> SEQ ID NO 23
<211> LENGTH: 8
<212> TYPE: PRT
```

-continued

```
<213> ORGANISM: Homo sapiens

<400> SEQUENCE: 23

Val Glu Met Asp Ala Ala Pro Gly
1               5

<210> SEQ ID NO 24
<211> LENGTH: 8
<212> TYPE: PRT
<213> ORGANISM: Homo sapiens

<400> SEQUENCE: 24

Val Ser Trp Asp Ser Gly Gly Ser
1               5

<210> SEQ ID NO 25
<211> LENGTH: 8
<212> TYPE: PRT
<213> ORGANISM: Homo sapiens

<400> SEQUENCE: 25

Glu Glu Thr Asp Gly Ile Ala Tyr
1               5

<210> SEQ ID NO 26
<211> LENGTH: 8
<212> TYPE: PRT
<213> ORGANISM: Homo sapiens

<400> SEQUENCE: 26

Val Glu Thr Asp Lys Ala Thr Val
1               5

<210> SEQ ID NO 27
<211> LENGTH: 8
<212> TYPE: PRT
<213> ORGANISM: Homo sapiens

<400> SEQUENCE: 27

Gly Ser Ser Asp Pro Leu Ile Gln
1               5

<210> SEQ ID NO 28
<211> LENGTH: 8
<212> TYPE: PRT
<213> ORGANISM: Homo sapiens

<400> SEQUENCE: 28

Asp Asp Ala Asp Tyr Lys Pro Lys
1               5

<210> SEQ ID NO 29
<211> LENGTH: 8
<212> TYPE: PRT
<213> ORGANISM: Homo sapiens

<400> SEQUENCE: 29

His Ile Ser Ser Leu Ile Lys Leu
1               5

<210> SEQ ID NO 30
<211> LENGTH: 8
<212> TYPE: PRT
<213> ORGANISM: Homo sapiens
```

```
<400> SEQUENCE: 30

Asp Pro Asn Asn Leu Leu Asn Asp
1               5

<210> SEQ ID NO 31
<211> LENGTH: 8
<212> TYPE: PRT
<213> ORGANISM: Homo sapiens

<400> SEQUENCE: 31

Asp Leu Ser Asp Leu Thr Ala Ala
1               5

<210> SEQ ID NO 32
<211> LENGTH: 8
<212> TYPE: PRT
<213> ORGANISM: Homo sapiens

<400> SEQUENCE: 32

Phe Ser Ala Tyr Ile Lys Asn Ser
1               5

<210> SEQ ID NO 33
<211> LENGTH: 8
<212> TYPE: PRT
<213> ORGANISM: Homo sapiens

<400> SEQUENCE: 33

Glu Ala Leu Pro Leu Leu Val Arg
1               5

<210> SEQ ID NO 34
<211> LENGTH: 8
<212> TYPE: PRT
<213> ORGANISM: Homo sapiens

<400> SEQUENCE: 34

Gln Gln Gly Ala Ile Gly Ser Pro
1               5

<210> SEQ ID NO 35
<211> LENGTH: 8
<212> TYPE: PRT
<213> ORGANISM: Homo sapiens

<400> SEQUENCE: 35

Gly Pro Pro Gly Ile Val Ile Gly
1               5

<210> SEQ ID NO 36
<211> LENGTH: 8
<212> TYPE: PRT
<213> ORGANISM: Homo sapiens

<400> SEQUENCE: 36

Met Asp Ile Ala Ile His His Pro
1               5

<210> SEQ ID NO 37
<211> LENGTH: 8
<212> TYPE: PRT
<213> ORGANISM: Homo sapiens

<400> SEQUENCE: 37
```

Phe Phe Lys Asn Ile Val Thr Pro
1               5

<210> SEQ ID NO 38
<211> LENGTH: 8
<212> TYPE: PRT
<213> ORGANISM: Homo sapiens

<400> SEQUENCE: 38

Gly Pro Leu Gly Ala Arg Gly Ile
1               5

<210> SEQ ID NO 39
<211> LENGTH: 8
<212> TYPE: PRT
<213> ORGANISM: Homo sapiens

<400> SEQUENCE: 39

His Leu Gly Gly Ala Lys Gln Val
1               5

<210> SEQ ID NO 40
<211> LENGTH: 8
<212> TYPE: PRT
<213> ORGANISM: Homo sapiens

<400> SEQUENCE: 40

Val Trp Ala Ala Glu Ala Ile Ser
1               5

<210> SEQ ID NO 41
<211> LENGTH: 8
<212> TYPE: PRT
<213> ORGANISM: Homo sapiens

<400> SEQUENCE: 41

Gly Pro Leu Gly Ala Arg Gly Ile
1               5

<210> SEQ ID NO 42
<211> LENGTH: 8
<212> TYPE: PRT
<213> ORGANISM: Homo sapiens

<400> SEQUENCE: 42

Glu Ser Gly Asp Tyr Lys Ala Thr
1               5

<210> SEQ ID NO 43
<211> LENGTH: 8
<212> TYPE: PRT
<213> ORGANISM: Homo sapiens

<400> SEQUENCE: 43

Val Ala Gln Asp Leu Asn Ala Pro
1               5

<210> SEQ ID NO 44
<211> LENGTH: 8
<212> TYPE: PRT
<213> ORGANISM: Homo sapiens

<400> SEQUENCE: 44

Ser Pro Asp Ala Leu Gln Asn Pro
1               5

```
<210> SEQ ID NO 45
<211> LENGTH: 8
<212> TYPE: PRT
<213> ORGANISM: Homo sapiens

<400> SEQUENCE: 45

Pro Pro Leu Lys Leu Met His Ser
1               5

<210> SEQ ID NO 46
<211> LENGTH: 8
<212> TYPE: PRT
<213> ORGANISM: Homo sapiens

<400> SEQUENCE: 46

Gly Pro His Leu Leu Val Glu Ala
1               5

<210> SEQ ID NO 47
<211> LENGTH: 8
<212> TYPE: PRT
<213> ORGANISM: Homo sapiens

<400> SEQUENCE: 47

Val Gly Pro Asn Leu His Gly Val
1               5

<210> SEQ ID NO 48
<211> LENGTH: 8
<212> TYPE: PRT
<213> ORGANISM: Homo sapiens

<400> SEQUENCE: 48

Gly Gly Gly Asn Lys Ile Gly Pro
1               5

<210> SEQ ID NO 49
<211> LENGTH: 8
<212> TYPE: PRT
<213> ORGANISM: Homo sapiens

<400> SEQUENCE: 49

Leu Ser Thr Ala Arg Phe Val Val
1               5

<210> SEQ ID NO 50
<211> LENGTH: 8
<212> TYPE: PRT
<213> ORGANISM: Homo sapiens

<400> SEQUENCE: 50

Val Thr Glu Asp Val Asp Ile Asn
1               5

<210> SEQ ID NO 51
<211> LENGTH: 8
<212> TYPE: PRT
<213> ORGANISM: Homo sapiens

<400> SEQUENCE: 51

Ser Ala Leu Ala Thr Thr Val Tyr
1               5
```

<210> SEQ ID NO 52
<211> LENGTH: 8
<212> TYPE: PRT
<213> ORGANISM: Homo sapiens

<400> SEQUENCE: 52

Gln Glu Leu Ile Ser Asn Ala Ser
1               5

<210> SEQ ID NO 53
<211> LENGTH: 8
<212> TYPE: PRT
<213> ORGANISM: Homo sapiens

<400> SEQUENCE: 53

Gln Glu Leu Ile Ser Asn Ala Ser
1               5

<210> SEQ ID NO 54
<211> LENGTH: 8
<212> TYPE: PRT
<213> ORGANISM: Homo sapiens

<400> SEQUENCE: 54

Trp Glu Leu Ile Ser Asn Ala Ser
1               5

<210> SEQ ID NO 55
<211> LENGTH: 8
<212> TYPE: PRT
<213> ORGANISM: Homo sapiens

<400> SEQUENCE: 55

Ser Gly Asn Tyr Ala Thr Val Ile
1               5

<210> SEQ ID NO 56
<211> LENGTH: 8
<212> TYPE: PRT
<213> ORGANISM: Homo sapiens

<400> SEQUENCE: 56

Ser Ile Gln Met Asn Val Ala Glu
1               5

<210> SEQ ID NO 57
<211> LENGTH: 8
<212> TYPE: PRT
<213> ORGANISM: Homo sapiens

<400> SEQUENCE: 57

Gln Gln Asn Tyr Gln Asn Ser Glu
1               5

<210> SEQ ID NO 58
<211> LENGTH: 8
<212> TYPE: PRT
<213> ORGANISM: Homo sapiens

<400> SEQUENCE: 58

Ser Ile Leu Arg Leu Ala Lys Ala
1               5

<210> SEQ ID NO 59
<211> LENGTH: 8

<212> TYPE: PRT
<213> ORGANISM: Homo sapiens

<400> SEQUENCE: 59

Lys Phe Gln Arg Ala Ile Thr Gly
1               5

<210> SEQ ID NO 60
<211> LENGTH: 8
<212> TYPE: PRT
<213> ORGANISM: Homo sapiens

<400> SEQUENCE: 60

Ala Glu Pro Lys Met His Lys Thr
1               5

<210> SEQ ID NO 61
<211> LENGTH: 8
<212> TYPE: PRT
<213> ORGANISM: Homo sapiens

<400> SEQUENCE: 61

Thr Ile Pro Arg Ala Ala Ile Asn
1               5

<210> SEQ ID NO 62
<211> LENGTH: 8
<212> TYPE: PRT
<213> ORGANISM: Homo sapiens

<400> SEQUENCE: 62

Ala Glu Phe Arg His Asp Ser Gly
1               5

<210> SEQ ID NO 63
<211> LENGTH: 8
<212> TYPE: PRT
<213> ORGANISM: Homo sapiens

<400> SEQUENCE: 63

Arg Arg Lys Arg Ile Val Gly Gly
1               5

<210> SEQ ID NO 64
<211> LENGTH: 8
<212> TYPE: PRT
<213> ORGANISM: Homo sapiens

<400> SEQUENCE: 64

Ala Met Ser Arg Met Ser Leu Ser
1               5

<210> SEQ ID NO 65
<211> LENGTH: 8
<212> TYPE: PRT
<213> ORGANISM: Homo sapiens

<400> SEQUENCE: 65

Pro Glu Pro Glu Gln Leu Lys Met
1               5

<210> SEQ ID NO 66
<211> LENGTH: 8
<212> TYPE: PRT
<213> ORGANISM: Homo sapiens

<400> SEQUENCE: 66

Gln Ser Lys Glu Ala Ile His Ser
1               5

<210> SEQ ID NO 67
<211> LENGTH: 8
<212> TYPE: PRT
<213> ORGANISM: Homo sapiens

<400> SEQUENCE: 67

Lys Leu Lys Glu Ala Ser Arg Ser
1               5

<210> SEQ ID NO 68
<211> LENGTH: 8
<212> TYPE: PRT
<213> ORGANISM: Homo sapiens

<400> SEQUENCE: 68

Arg Ala Lys Arg Ser Pro Lys His
1               5

<210> SEQ ID NO 69
<211> LENGTH: 8
<212> TYPE: PRT
<213> ORGANISM: Homo sapiens

<400> SEQUENCE: 69

Arg Lys Lys Arg Ser Thr Ser Ala
1               5

<210> SEQ ID NO 70
<211> LENGTH: 8
<212> TYPE: PRT
<213> ORGANISM: Homo sapiens

<400> SEQUENCE: 70

Ser Ala Met Ala Ala Asp Ser Asn
1               5

<210> SEQ ID NO 71
<211> LENGTH: 8
<212> TYPE: PRT
<213> ORGANISM: Homo sapiens

<400> SEQUENCE: 71

Thr Leu Leu Ala Asn Ile Asn Glu
1               5

<210> SEQ ID NO 72
<211> LENGTH: 8
<212> TYPE: PRT
<213> ORGANISM: Homo sapiens

<400> SEQUENCE: 72

Gln Ala Glu Glu Thr Tyr Glu Asn
1               5

<210> SEQ ID NO 73
<211> LENGTH: 8
<212> TYPE: PRT
<213> ORGANISM: Homo sapiens

<400> SEQUENCE: 73

```
Asp Val Ile Asp Met Ser Lys Glu
1               5

<210> SEQ ID NO 74
<211> LENGTH: 8
<212> TYPE: PRT
<213> ORGANISM: Homo sapiens

<400> SEQUENCE: 74

Glu Val Leu Ala Thr Pro Pro Ala
1               5

<210> SEQ ID NO 75
<211> LENGTH: 8
<212> TYPE: PRT
<213> ORGANISM: Homo sapiens

<400> SEQUENCE: 75

Ala Pro Val Pro Gly Thr Ala Trp
1               5
```

ACTIVITY SENSOR WITH TUNABLE ANALYTE

CROSS-REFERENCE TO RELATED APPLICATION

This application claims the benefit of U.S. Provisional Application Ser. No. 62/682,492, filed Jun. 8, 2018, the contents of which are incorporated by reference.

SEQUENCE LISTING

This instant application contains a Sequence Listing which has been submitted electronical in ASCII format and is hereby incorporated by reference in its entirety. Said ASCII copy, created on May 31, 2023, is named 61226_704_201_SL.txt and is 10,830 bytes in size.

TECHNICAL FIELD

The invention relates to a tunable analyte for characterizing a physiological state.

BACKGROUND

Current approaches to detecting or diagnosing diseases such as cancer involve techniques such as obtaining a tissue biopsy and examining cells under a microscope or sequencing DNA to detect genetic markers of the disease. It is thought that early detection is advantageous because some treatments will have a greater chance of success with early intervention. For example, with cancer, a tumor may be surgically removed and a patient may go into full remission if the cancer is detected before it spreads throughout the body in a process known as metastasis. Medical consensus is that favorable outcomes such as full remission after tumor resection require early detection.

Unfortunately, existing approaches to disease detection do not always detect a disease at its incipiency. For example, while x-ray mammogram represents an advance over manual examination in that an x-ray may detect a tumor that cannot be detected by physical examination. Such tests nevertheless require a tumor to have progressed to some degree for detection to occur. Liquid biopsy represents one potential method for disease detection. In a liquid biopsy, a blood sample is taken and screened for small fragments of tumor DNA. Unfortunately, x-ray mammogram, microscopic examination of tissue samples, and liquid biopsy only detect disease that has advance to some degree and do not always detect disease as early as would be most medically beneficial.

SUMMARY

The invention provides activity sensors useful for non-invasively detecting activity characteristic of a physiological state, such as a disease state. The activity sensors include a molecular carrier structure linked to several cleavable, detectable analytes via cleavable linkers. The linkers are susceptible to cleavage by enzymes that are differentially expressed under a physiological state of interest. For example, the activity sensors may be a multi-arm polyethylene glycol (PEG) scaffold linked to four or more polypeptide reporters as the cleavable analytes. The cleavable linkers are specific for different enzymes whose activity is characteristic of a condition of tissue. When administered to a patient, the activity sensors locate to a target tissue, where they are cleaved by the enzymes to release the detectable analytes. The analytes are detected in a patient sample such as a urine sample. The detected analytes serve as a report of which enzymes are active in the tissue.

Because enzymes are differentially expressed under the physiological state of interest such as a disease stage or degree of disease progression, analysis of the sample provides a non-invasive test for the physiological state (e.g., disease stage or condition) of the organ, bodily compartment, bodily fluid, or tissue. The carrier structure preferably includes multiple molecular subunits and may be, for example, a multi-arm polyethylene glycol (PEG) polymer, a lipid nanoparticle, or a dendrimer. The detectable analytes may be, for example, polypeptides that are cleaved by proteases that are differentially expressed in tissue or organs under a specified physiological state, e.g., affected by disease. Because the carrier structure and the detectable analytes are biocompatible molecular structures that locate to a target tissue and are cleaved by disease-associated enzymes to release analytes detectable in a sample, compositions of the disclosure provide non-invasive methods for detecting and characterizing a disease state or stage of an organ or tissue. Because the compositions provide substrates that are released as detectable analytes by enzymatic activity, quantitative detection of the analytes in the sample provide a measure of rate of activity of the enzymes in the organ or tissue. Thus methods and compositions of the disclosure provide non-invasive techniques for measuring both stage and rate of progression of a disease or condition in a target organ or tissue.

Additionally, the activity sensors may include additional molecular structures to influence trafficking of the sensors within the body, or timing of the enzymatic cleavage or other metabolic degradation of the particles. The molecular structures may function as tuning domains, additional molecular subunits or linkers that are acted upon by the body to locate the activity sensor to the target tissue under controlled timing. For example, the tuning domain may modulate the particle's fate by protecting the activity sensor from premature cleavage and indiscriminate hydrolysis, shielding the particle from immune detection and clearance, or by targeting the particle to specific tissue or cell types. Trafficking may be influenced by including additional molecular structures in the core carrier polymer by, for example, increasing a size of a PEG scaffold to slow degradation of the particle in the body.

The invention provides a tunable activity sensor that reveals enzymatic activity associated with a physiological state such as disease. When the activity reporter is administered to a patient, it is trafficked through the body to specific cells or specific tissues. Alternatively, the sensor may be designed or tuned so that it remains in circulation, e.g., in blood, or lymph, or both. If enzymes that are differentially expressed under conditions of a particular disease are present, those enzymes cleave the reporter and release a detectable analyte. Because the analytes are linked to the carrier/scaffold by cleavage targets of enzymes known to be active in tissue affected by a disease, detection of the analyte is indicative of the disease condition. For example, when the activity sensor includes cleavage targets of proteases expressed in liver fibrosis, the sensor is cleaved in the liver to release the detectable analyte into circulation after which renal filtration excretes the detectable analyte in urine. Presence of the analyte in a urine sample from the patient is a signature of liver fibrosis in the patient.

Molecular structures can be included in the activity sensor as tuning domains, to tune or modify a distribution or residence time of the activity sensor within the subject. The tuning domains may be linked to the carrier/scaffold or to the detectable analyte and may be modified in numerous ways. Through the use of tuning domains, one may modify the activity sensor's distribution within the body depending on in vivo trafficking pathways to a specific tissue, or its residence time within systemic circulation or within a specific tissue. Additionally, the tuning domains may promote effective cleavage of the reporter by tissue-specific enzymes or prevent premature cleavage or hydrolysis.

Activity sensors according to the disclosure provide a sensitive and non-invasive method for detecting disease-associated activity. The activity sensors are acted upon in the body of the patient so that the detectable analyte is released in such a manner as to indicate critical disease states at a very early stage. The activity sensors may include additional molecular structures as tuning domains that employ the body for sample preparation by presenting a molecular complex that only releases the detectable analyte into a collectable sample when the body processes the activity sensor in a detectable manner. The tuning domains allow for precise tuning of the biological fate of the activity sensor. Additionally, because the detectable analytes are the product of enzymatic activity and the activity sensors can be provided in excess, the signal given by the analyte is effectively amplified, and the presence of even very small quantity of active enzyme may be detected. Because the tuning domains can target the activity sensor to specific tissue of the body and because the reporter is known to be cleaved by enzymes associated with a disease, the activity sensors provide for very rapid and sensitive disease detection.

In certain aspects, the invention provides compositions that include activity sensors. The activity sensors include a carrier comprising a plurality of molecular subunits and a plurality of detectable reporters, each linked to the carrier by a cleavable linker containing the cleavage site of an enzyme. The activity sensor reports activity of a plurality of distinct enzymes by releasing the reporters upon cleavage by the enzymes. In some embodiments, the carrier comprises a poly ethylene glycol (PEG) scaffold of covalently linked PEG subunits. The activity sensor preferably includes at least four distinct detectable reporters, linked via at least four distinct, enzyme-specific cleavage sites to report activity of at least four corresponding enzymes. Each detectable reporter and cleavable linker may be provided by a polypeptide susceptible to cleavage by a protease. The activity sensors may further include a molecular structure or tuning domain that modifies a distribution or residence time of the activity sensor within a subject when administered to the subject.

In some embodiments, the tuning domains comprise ligands for receptors of a specific cell or a specific tissue type. When the activity sensor is administered to a subject, the ligands promote accumulation of the activity sensor in the specific tissue type. Each ligand may be, for example, a small molecule, a peptide, an antibody or a fragment of an antibody, a nucleic acid, or an aptamer. In certain embodiments, the ligands are peptides conjugated to the scaffold via maleimide-thiol coupling or amide bonds.

In certain embodiments, the biocompatible scaffold includes multiple subunits of covalently linked poly(ethylene glycol) (PEG) maleimide, and has a molecular weight between about 10 and about 80 kDa (preferably between 20 and 40, e.g., about 40 kDa). The tuning domains may be ligands that bind to receptors of a specific cell or tissue type, thereby promoting accumulation of the activity sensor in the specific tissue type.

In some embodiments, the activity sensor includes a plurality of tuning domains in the form of hydrophobic chains that facilitate diffusion of the activity sensor across a cell membrane. For example, the activity sensor may include both peptide ligands for receptors of specific cell or tissue type and hydrophobic chains that facilitate diffusion of the activity sensor across a cell membrane. In certain embodiments, the tuning domains include cell-penetrating domains such as, for example, poly-arginine peptides or stapled peptides. In other embodiments, the activity sensor is designed to remain circulating in, for example, blood, lymph, or both.

The activity sensor may have the tuning domains linked to the reporters. For example, the tuning domains may be linked such that they are associated with the detectable analyte after cleavage. The activity sensor may include a plurality of reporters and a plurality of tuning domains, wherein the tuning domains comprise biocompatible polymer linked to the reporters. The carrier may include multiple subunits of covalently linked PEG maleimide, with the reporters including peptide chains susceptible to cleavage by one or more enzymes. The tuning domains may be included as biocompatible polymers extending from the peptide chains to protect the activity sensor from in vivo degradation, thereby increasing a serum half-life of the activity sensor when administered to a patient relative to a activity sensor lacking the tuning domains.

In certain embodiments, the carrier comprises a biocompatible scaffold, the reporters comprise polypeptides susceptible to cleavage by one or more proteases, and the tuning domains comprises polymers that shield the polypeptides from immune detection or inhibit cellular uptake of the activity sensor by macrophages. The polypeptides may include sequences susceptible to cleavage by proteases known to be associated with a specific disease and the tuning domain polymers may include comprise PEG side chains.

The activity sensor may include a carrier that uses a bio-compatible scaffold of about 20 to 50 kDa (preferably between about 30 and 45 kDa) linked to reporters with polypeptides susceptible to cleavage by one or more proteases, in which the tuning domains are polymers between the scaffold and the polypeptides. In some embodiments, the tuning domains add space between the carrier and the reporters, to decrease steric hindrance among parts of the activity sensor and thereby increase accessibility of the polypeptides to the proteases to promote successful cleavage.

In certain embodiments, the carrier is a bio-compatible scaffold, the reporters include polypeptides susceptible to cleavage by one or more proteases, and the tuning domains are provided as regions of the polypeptides that include D-amino acids to prevent proteolytic cleavage of the regions. Delivery of the activity sensor to tissue of a subject affected by the disease results in cleavage of the polypeptide and release of an analyte detectable in a sample from the subject, while the D-amino acids protect the analyte from digestion until detection. In some embodiments, a cleavage site of the polypeptides in tissue of a specific type is determined by a composition or relative order of the L- and D-amino acids in the polypeptides.

In preferred embodiments, the reporter comprises a polypeptide that is cleaved from the activity sensor by proteases associated with a disease and tuning domains comprise one or more polymers on the polypeptide that facilitate passage of the reporter into systemic circulation after cleavage. The reporter may include a polypeptide that is liberated from the activity sensor by proteases associated with a disease and the tuning domains may include one or more polymers on the polypeptide that inhibit enzymatic activity upon the liberated reporter prior to excretion from the subject.

The tuning domain may be a biocompatible polymer that protects the activity sensor from immune detection and clearance. The reporter may be one or more of a volatile organic compound, an elemental mass tag, a peptide comprising one or more D-amino acids, a nucleic acid, or a neoantigen. The reporter may be an elemental mass tag (e.g., a molecular chelator with an element, preferably of atomic number greater than 20 to distinguish from common biological elements, e.g., in mass spectrometry). In certain embodiments, the reporter comprises an antigen detectable by a hybridization assay. In some embodiments, the carrier is a bio-compatible scaffold and the reporter includes at least one polypeptide susceptible to cleavage by a protease to release a detectable analyte, and the tuning domain forms a portion of the detectable analyte.

DETAILED DESCRIPTION

Figure 1:
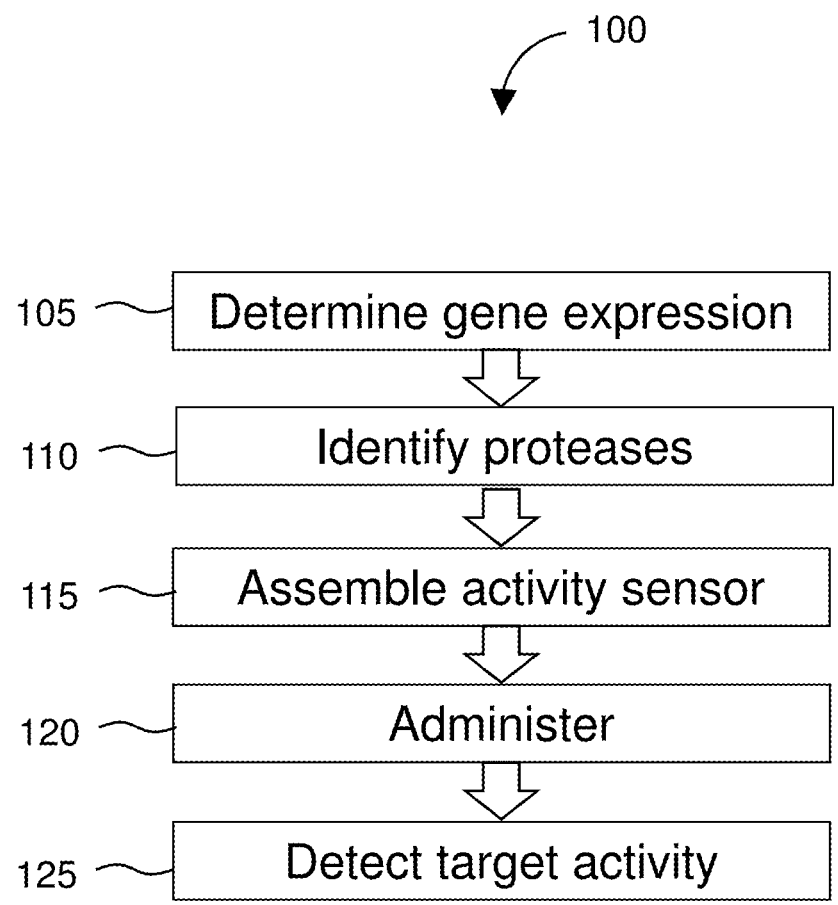
FIG. 1 diagrams steps of a method for designing an activity sensor.

The invention provides an activity sensor that includes a carrier, at least one reporter linked to the carrier and at least one tuning domain that modifies a distribution or residence time of the activity sensor within a subject when administered to the subject. The activity sensor may be designed to detect and report any enzymatic activity in the body, for example, enzymes that are differentially expressed under a physiological state of interest such as dysregulated protease activity indicative of a disease state. Dysregulated proteases have important consequences in the progression of diseases such as cancer in that they may alter cell signaling, help drive cancer cell proliferation, invasion, angiogenesis, avoidance of apoptosis, and metastasis.

The activity sensor may be tuned via the tuning domains in numerous ways to facilitate detecting enzymatic activity within the body in specific cells or in a specific tissue. For example, the activity sensor may be tuned to promote distribution of the activity sensor to the specific tissue or to improve a residence time of the activity sensor in the subject or in the specific tissue.

When administered to a subject, the activity sensor is trafficked through the body and may diffuse from the systemic circulation to a specific tissue, where the reporter may be cleaved via enzymes indicative of the disease to release a detectable analyte. The detectable analyte may then diffuse back into circulation where it may pass renal filtration and be excreted into urine, whereby detection of the detectable analyte in the urine sample indicates enzymatic activity upon the reporter.

The carrier may be any suitable platform for trafficking the reporters through the body of a subject, when administered to the subject. The carrier may be any material or size suitable to serve as a carrier or platform. Preferably the carrier is biocompatible, non-toxic, and non-immunogenic and does not provoke an immune response in the body of the subject to which it is administered. The carrier may also function as a targeting means to target the activity sensor to a tissue, cell or molecule. In some embodiments the carrier domain is a particle such as a polymer scaffold. The carrier may, for example, result in passive targeting to tumors or other specific tissues by circulation. Other types of carriers include, for example, compounds that facilitate active targeting to tissue, cells or molecules. Examples of carriers include, but are not limited to, nanoparticles such as iron oxide or gold nanoparticles, aptamers, peptides, proteins, nucleic acids, polysaccharides, polymers, antibodies or antibody fragments and small molecules.

The carrier may include a variety of materials such as iron, ceramic, metallic, natural polymer materials such as hyaluronic acid, synthetic polymer materials such as polyglycerol sebacate, and non-polymer materials, or combinations thereof. The carrier may be composed in whole or in part of polymers or non-polymer materials, such as alumina, calcium carbonate, calcium sulfate, calcium phosphosilicate, sodium phosphate, calcium aluminate, and silicates. Polymers include, but are not limited to: polyamides, polycarbonates, polyalkylenes, polyalkylene glycols, polyalkylene oxides, cellulose ethers, cellulose esters, nitro celluloses, polymers of acrylic and methacrylic esters, methyl cellulose, ethyl cellulose, and hydroxypropyl cellulose. Examples of non-biodegradable polymers include ethylene vinyl acetate, poly(meth) acrylic acid, polyamides, copolymers and mixtures thereof.

Examples of biodegradable polymers include synthetic polymers such as polymers of lactic acid and glycolic acid, poly-anhydrides, polyurethanes, and natural polymers such as alginate and other polysaccharides including dextran and cellulose, collagen, albumin and other proteins, copolymers and mixtures thereof. In general, these biodegradable polymers degrade either by enzymatic hydrolysis or exposure to water in vivo, by surface or bulk erosion. These biodegradable polymers may be used alone, as physical mixtures (blends), or as co-polymers.

In preferred embodiments, the carrier includes biodegradable polymers so that whether the reporter is cleaved from the carrier, the carrier will be degraded in the body. By providing a biodegradable carrier, accumulation and any associated immune response or unintended effects of intact activity sensors remaining in the body may be minimized.

Other biocompatible polymers include PEG, PVA and PVP, which are all commercially available. PVP is a non ionogenic, hydrophilic polymer having a mean molecular weight ranging from approximately 10,000 to 700,000 and has the chemical formula (C6H9NO)[n]. PVP is also known as poly[1 (2 oxo 1 pyrrolidinyl)ethylene]. PVP is nontoxic, highly hygroscopic and readily dissolves in water or organic solvents.

Polyvinyl alcohol (PVA) is a polymer prepared from polyvinyl acetates by replacement of the acetate groups with hydroxyl groups and has the chemical formula (CH2CHOH)[n]. Most polyvinyl alcohols are soluble in water.

Polyethylene glycol (PEG), also known as poly(oxyethylene) glycol, is a condensation polymer of ethylene oxide and water. PEG refers to a compound that includes repeating ethylene glycol units. The structure of PEG may be expressed as H—(O—CH2-CH2)n-OH. PEG is a hydrophilic compound that is biologically inert (i.e., non-immunogenic) and generally considered safe for administration to humans.

When PEG is linked to a particle, it provides advantageous properties, such as improved solubility, increased circulating life, stability, protection from proteolytic degradation, reduced cellular uptake by macrophages, and a lack of immunogenicity and antigenicity. PEG is also highly flexible and provides bio-conjugation and surface treatment of a particle without steric hindrance. PEG may be used for chemical modification of biologically active compounds, such as peptides, proteins, antibody fragments, aptamers, enzymes, and small molecules to tailor molecular properties of the compounds to particular applications. Moreover, PEG molecules may be functionalized by the chemical addition of various functional groups to the ends of the PEG molecule, for example, amine-reactive PEG (BS (PEG)n) or sulfhydryl-reactive PEG (BM (PEG)n).

In certain embodiments, the carrier is a biocompatible scaffold, such as a scaffold including polyethylene glycol (PEG). In a preferred embodiment, the carrier is a biocompatible scaffold that includes multiple subunits of covalently linked poly(ethylene glycol) maleimide (PEG-MAL), for example, an 8-arm PEG-MAL scaffold. A PEG-containing scaffold may be selected because it is biocompatible, inexpensive, easily obtained commercially, has minimal uptake by the reticuloendothelial system (RES), and exhibits many advantageous behaviors. For example, PEG scaffolds inhibit cellular uptake of particles by numerous cell types, such as macrophages, which facilitates proper distribution to a specific tissues and increases residence time in the tissue.

An 8-arm PEG-MAL is a type of multi-arm PEG derivative that has maleimide groups at each terminal end of its eight arms, which are connected to a hexaglycerol core. The maleimide group selectively reacts with free thiol, SH, sulfhydryl, or mercapto group via Michael addition to form a stable carbon sulfur bond. Each arm of the 8-arm PEG-MAL scaffold may be conjugated to peptides, for example, via maleimide-thiol coupling or amide bonds.

The PEG-MAL scaffold may be of various sizes, for example, a 10 kDa scaffold, a 20 kDa scaffold, a 40 kDa scaffold, or a greater than 40 kDa scaffold. The hydrodynamic diameter of the PEG scaffold in phosphate buffered saline (PBS) may be determined by various methods known in the art, for example, by dynamic light scattering. Using such techniques, the hydrodynamic diameter of a 40 kDa PEG-MAL scaffold was measured to be approximately 8 nm. In preferred embodiments, a 40 kDa PEG-MAL scaffold is provided as the carrier when the activity sensor is administered subcutaneously because the activity sensor readily diffuses into systemic circulation but is not readily cleared by the reticuloendothelial system.

The size of the PEG-MAL scaffold affects the distribution and residence time of the activity sensor in the body because particles smaller than about 5 nm in diameter are efficiently cleared through renal filtration of the body, even without proteolytic cleavage. Further, particles larger than about 10 nm in diameter often drain into lymphatic vessels. In one example, where a 40 kDa 8-arm PEG-MAL scaffold was administered intravenously, the scaffold was not renally cleared into urine.

The reporter may be any reporter susceptible to an enzymatic activity, such that cleavage of the reporter indicates that enzymatic activity. The reporter is dependent on enzymes that are active in a specific disease state. For example, tumors are associated with a specific set of enzymes. For a tumor, the activity sensor may be designed with an enzyme susceptible site that matches that of the enzymes expressed by the tumor or other diseased tissue. Alternatively, the enzyme-specific site may be associated with enzymes that are ordinarily present but are absent in a particular disease state. In this example, a disease state would be associated with a lack of signal associated with the enzyme, or reduced levels of signal compared to a normal reference or prior measurement in a healthy subject.

In various embodiments, the reporter includes a naturally occurring molecule such as a peptide, nucleic acid, a small molecule, a volatile organic compound, an elemental mass tag, or a neoantigen. In other embodiments, the reporter includes a non-naturally occurring molecule such as D-amino acids, synthetic elements, or synthetic compounds. The reporter may be a mass-encoded reporter, for example, a reporter with a known and individually-identifiable mass, such as a polypeptide with a known mass or an isotope.

An enzyme may be any of the various proteins produced in living cells that accelerate or catalyze the metabolic processes of an organism. Enzymes act on substrates. The substrate binds to the enzyme at a location called the active site before the reaction catalyzed by the enzyme takes place. Generally, enzymes include but are not limited to proteases, glycosidases, lipases, heparinases, phosphatases. Examples of enzymes that are associated with disease in a subject include but are not limited to MMP, MMP-2, MMP-7, MMP-9, kallikreins, cathepsins, seprase, glucose-6-phosphate dehydrogenase (G6PD), glucocerebrosidase, pyruvate kinase, tissue plasminogen activator (tPA), a disintegrin and metalloproteinase (ADAM), ADAMS, ADAM15, and matriptase.

Examples of substrates for disease-associated enzymes include but are not limited to Interleukin 1 beta, IGFBP-3, TGF-beta, TNF, FASL, HB-EGF, FGFR1, Decorin, VEGF, EGF, IL2, IL6, PDGF, fibroblast growth factor (FGF), and tissue inhibitors of MMPs (TIMPs).

The disease or condition detected by the activity sensor may be any disease or condition that is associated with an enzymatic activity. For example, cancer progression and metastasis, cardiovascular disease, liver fibrosis, nonalcoholic fatty liver disease (NAFLD), arthritis, viral, bacterial, parasitic or fungal infection, Alzheimer's disease emphysema, thrombosis, hemophilia, stroke, organ dysfunction, any inflammatory condition, vascular disease, parenchymal disease, or a pharmacologically-induced state are all known to be associated with enzymatic activity.

The tuning domains may include any suitable material that modifies a distribution or residence time of the activity sensor within a subject when the activity sensor is administered to the subject. For example, the tuning domains may include PEG, PVA, or PVP. In another example, the tuning domains may include a polypeptide, a peptide, a nucleic acid, a polysaccharide, volatile organic compound, hydrophobic chains, or a small molecule.

FIG. 1 diagrams steps of a method 100 for designing an activity sensor. At step 105, gene expression in subjects with a known disease may be determined, for example, by performing RNA sequencing (RNA-Seq) on gene transcripts using a next-generation sequencing platform, and determining fold-change in expression level of a transcript associated with the disease by normalizing read counts from the measured transcripts against healthy control read counts.

At step 110, for example, gene expression that is upregulated in relation to a non-diseased state may be determined, for example, to identify candidate proteases indicative of a disease. By identifying candidate proteases indicative of the disease, associated protease substrates may also be identified and incorporated into the reporter of the activity sensor.

At step 115, an activity sensor including a carrier, at least one reporter linked to the carrier, and at least one tuning domain may be assembled.

Figure 2:
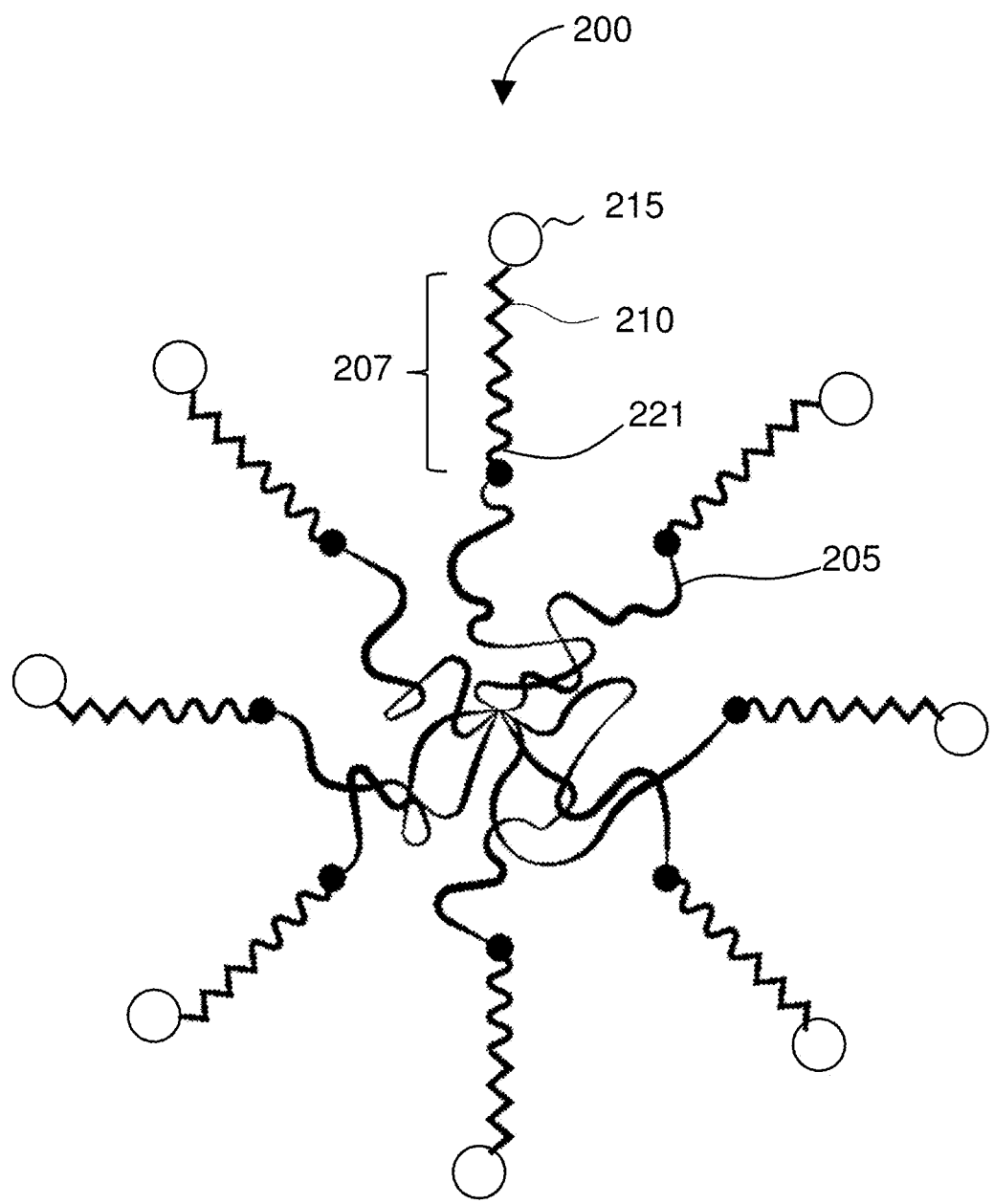
FIG. 2 shows an activity sensor.

FIG. 2 shows an activity sensor 200 with carrier 205, reporters 207, and tuning domains 215. As illustrated, carrier 205 is a biocompatible scaffold that includes multiple subunits of covalently linked poly(ethylene glycol) maleimide (PEG-MAL). Carrier 205 is an 8-arm PEG-MAL scaffold with a molecular weight between about 20 and 80 kDa. Reporter 207 is a polypeptide including a region susceptible to an identified protease. Activity of the identified protease to cleave the reporter indicates the disease. Reporter 207 includes a cleavable substrate 221 connected to detectable analyte 210. When a cleavage by the identified protease occurs upon cleavable substrate 221, detectable analyte 210 is released from activity sensor 200 and may pass out of the tissue, excreted from the body and detected.

Figure 3:
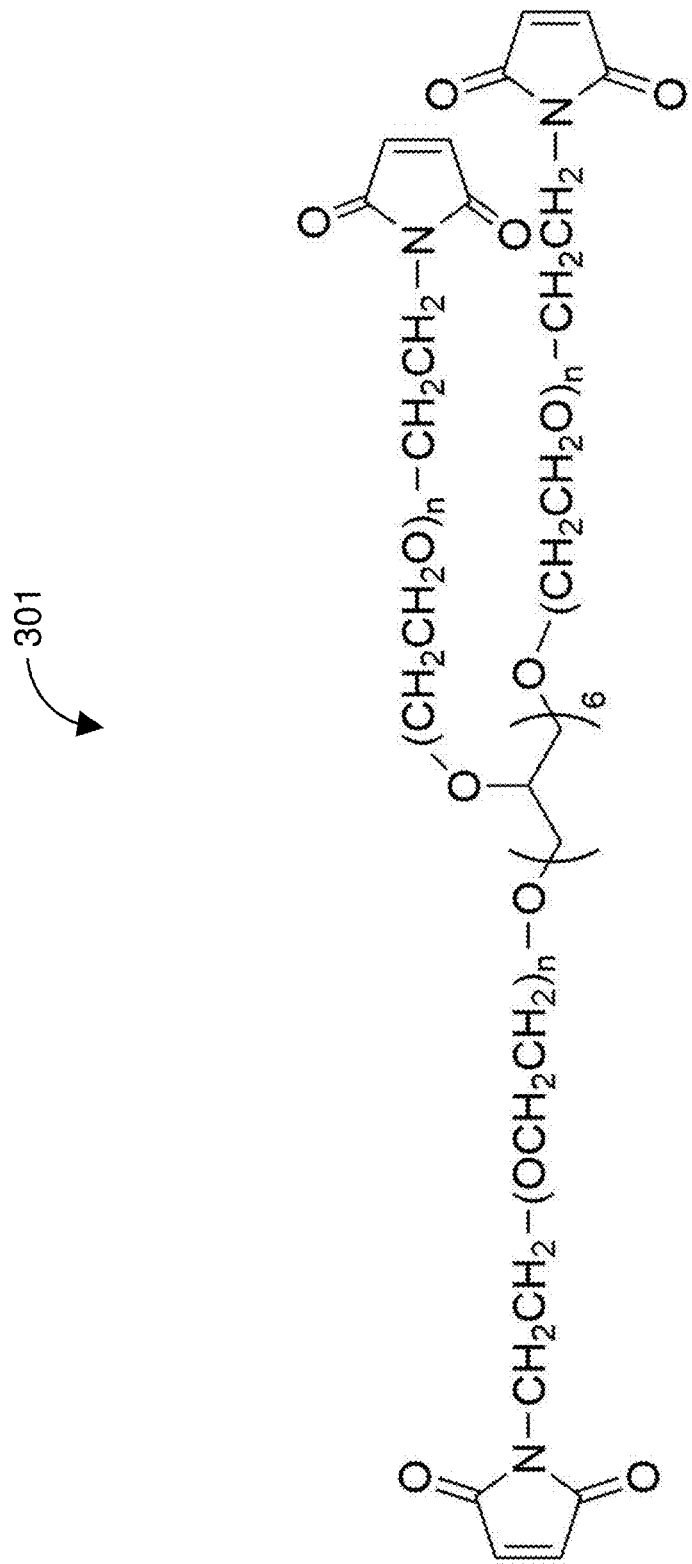
FIG. 3 shows poly(ethylene glycol)-maleimide (PEG-MAL).

FIG. 3 shows a poly(ethylene glycol)-maleimide (PEG-MAL) molecule 301 with eight arms, each with a maleimide (H2C2(CO)2NH) group at each terminal end. The maleimide group crosslinks specifically and efficiently with sulfhydryl (—SH) groups in peptides and other thiol molecules. As such, polypeptides may be linked to each of the maleimide groups at the ends of each arm of the PEG-MAL molecule, for example, via maleimide-thiol coupling or amide bonds.

Figure 4:
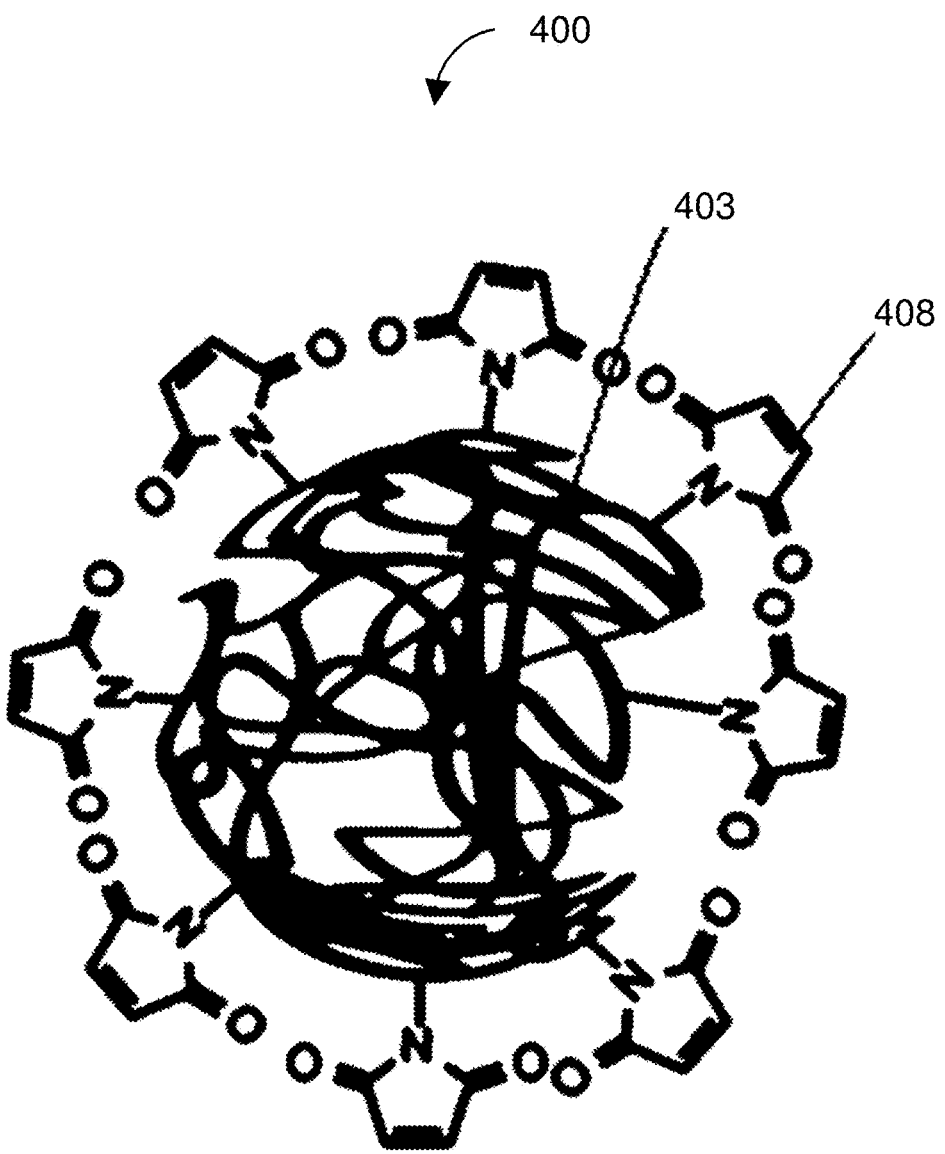
FIG. 4 shows an 8-arm PEG-MAL scaffold.

FIG. 4 shows a carrier that is an 8-arm PEG-MAL scaffold 400. The 8-arm PEG-MAL scaffold is composed of PEG-MAL. The carrier includes a center region 403 and maleimide groups 408 positioned around the center region 403.

The reporter may be any suitable reporter, such as a polypeptide susceptible to the protease activity as identified in step 110. Tuning domains may be linked to the activity sensor based on the in vivo pathway through which the activity sensor is to be trafficked or the intended method of detection. For example, the tuning domains may be PEG and linked to the activity sensor to facilitate distribution of the activity sensor to the liver to detect protease activity in the liver, and the reporter may be detected via a ligand binding assay, such as an ELISA assay.

At step 120, the activity sensor may be administered to a subject having the disease to detect enzymatic activity indicative of the disease, such as dysregulated protease activity.

The activity sensor may be administered by any suitable method of delivery. In preferred embodiments, the activity sensor is delivered intravenously or aerosolized and delivered to the lungs, for example, via a nebulizer. In other examples, the activity sensor may be administered to a subject transdermally, intradermally, intraarterially, intralesionally, intratumorally, intracranially, intraarticularly, intratumorally, intramuscularly, subcutaneously, orally, topically, locally, inhalation, injection, infusion, or by other method or any combination known in the art (see, for example, Remington's Pharmaceutical Sciences (1990), incorporated by reference).

At step 125, the target enzymatic activity may be detected in any biological sample. In preferred embodiments, the biological sample is non-invasively obtained and is preferably a bodily fluid or other substance that is naturally excreted from the body.

When the activity sensor enters the diseased microenvironment, for example tissues of a diseased liver or kidney, proteases with activity specific to the reporter polypeptide cleave the polypeptide, liberating the reporter from the carrier. The liberated reporter may then re-enter circulation and pass through renal filtration to urine or otherwise excreted in any manner from the tissue and from the subject having the disease. The reporter may then be detected from the excreted sample in any suitable manner, for example, by mass spectrometry or a ligand binding assay, such as an ELISA-based assay. By detecting the liberated reporter in the sample, the presence of enzymatic activity upon the activity sensor is shown, thereby detecting the target enzymatic activity.

Figure 5:
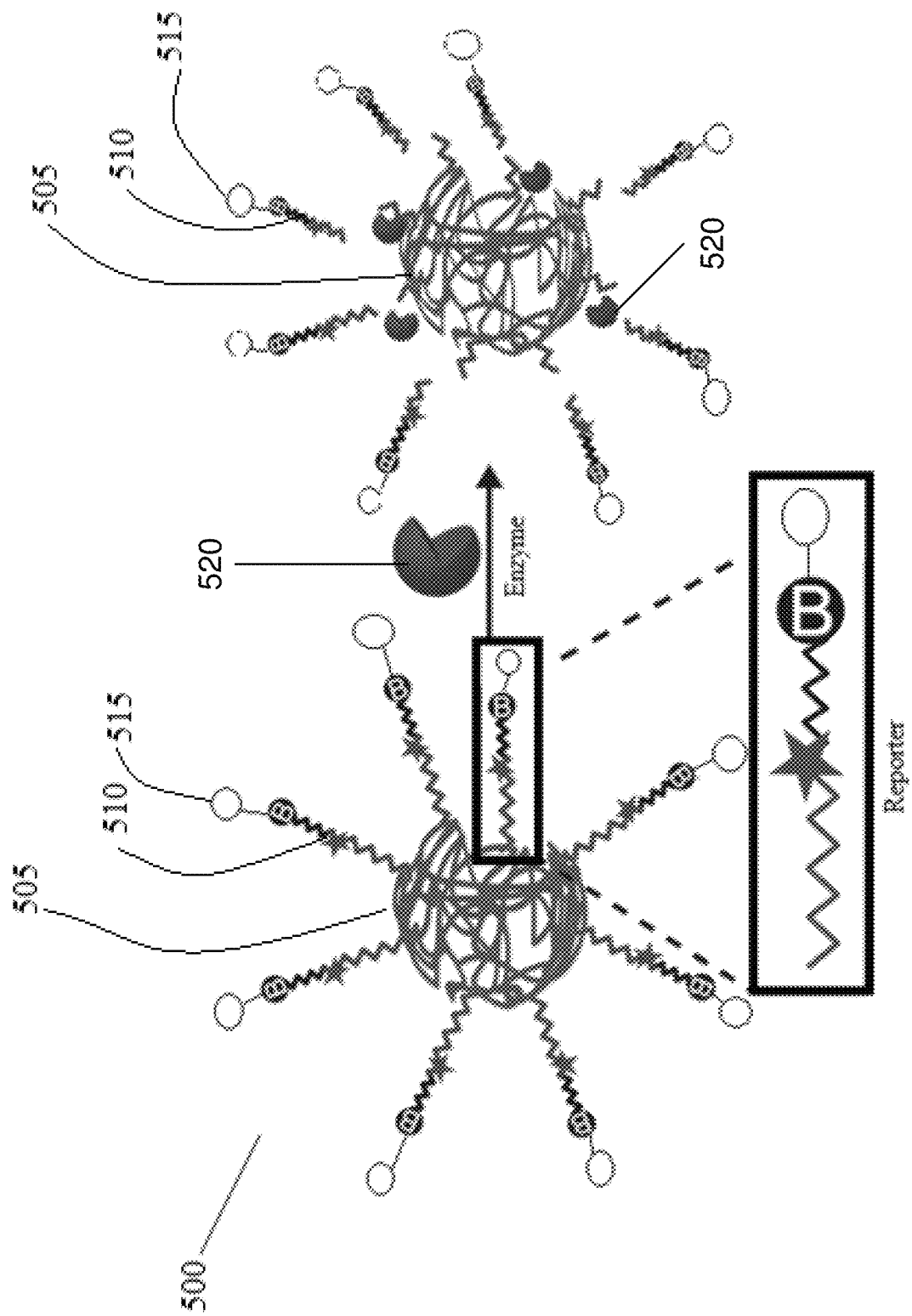
FIG. 5 illustrates a reaction between an enzyme and the activity sensor.

FIG. 5 illustrates a reaction between an enzyme 520 and the activity sensor 500. As shown, activity sensor 500 includes a carrier 505, a reporter 510, and tuning domains 515. Enzyme 520 cleaves each of the reporters 510 at enzymatically susceptible sites, liberating the reporters 510 from carrier 505. In one example, the reporter includes a polypeptide that is a substrate for a protease dysregulated when a disease is present. The protease cleaves the reporter from the carrier and, once released, reporters 510 may diffuse away from carrier 505 and may re-enter circulation to be excreted and detected.

The detected enzymatic activity may be activity of any type of enzyme, for example, proteases, kinases, esterases, peptidases, amidases, oxidoreductases, transferases, hydrolases, lysases, isomerases, or ligases.

The biological sample may be any sample from a subject in which the reporter may be detected. For example, the sample may be a tissue sample (such as a blood sample, a hard tissue sample, a soft tissue sample, etc.), a urine sample, saliva sample, mucus sample, fecal sample, seminal fluid sample, or cerebrospinal fluid sample.

Reporter Detection

The reporter may be detected by any suitable detection method able to detect the presence of quantity of molecules within the detectable analyte, directly or indirectly. For example, reporters may be detected via a ligand binding assay, which is a test that involves binding of the capture ligand to an affinity agent. Reporters may be directly detected, following capture, through optical density, radioactive emissions, nonradiative energy transfers. Alternatively, reporters may be indirectly detected with antibody conjugates, affinity columns, streptavidin-biotin conjugates, PCR analysis, DNA microarray, or fluorescence analysis.

A ligand binding assay often involves a detection step, such as an ELISA, including fluorescent, colorimetric, bioluminescent and chemiluminescent ELISAs, a paper test strip or lateral flow assay, or a bead-based fluorescent assay.

In one example, a paper-based ELISA test may be used to detect the liberated reporter in urine. The paper-based ELISA may be created inexpensively, such as by reflowing wax deposited from a commercial solid ink printer to create an array of test spots on a single piece of paper. When the solid ink is heated to a liquid or semi-liquid state, the printed wax permeates the paper, creating hydrophobic barriers. The space between the hydrophobic barriers may then be used as individual reaction wells. The ELISA assay may be performed by drying the detection antibody on the individual reaction wells, constituting test spots on the paper, followed by blocking and washing steps. Urine from the urine sample taken from the subject may then be added to the test spots, then streptavidin alkaline phosphate (ALP) conjugate may be added to the test spots, as the detection antibody. Bound ALP may then be exposed to a color reacting agent, such as BCIP/NBT (5-bromo-4-chloro-3'-indolyphosphate p-toluidine salt/nitro-blue tetrazolium chloride), which causes a purple colored precipitate, indicating presence of the reporter.

In another example, volatile organic compounds may be detected by analysis platforms such as gas chromatography instrument, a breathalyzer, a mass spectrometer, or use of optical or acoustic sensors.

Gas chromatography may be used to detect compounds that can be vaporized without decomposition (e.g., volatile organic compounds). A gas chromatography instrument includes a mobile phase (or moving phase) that is a carrier gas, for example, an inert gas such as helium or an unreactive gas such as nitrogen, and a stationary phase that is a microscopic layer of liquid or polymer on an inert solid support, inside a piece of glass or metal tubing called a column. The column is coated with the stationary phase and the gaseous compounds analyzed interact with the walls of the column, causing them to elute at different times (i.e., have varying retention times in the column). Compounds may be distinguished by their retention times.

A modified breathalyzer instrument may also be used to detect volatile organic compounds. In a traditional breathalyzer that is used to detect an alcohol level in blood, a subject exhales into the instrument, and any ethanol present in the subject's breath is oxidized to acetic acid at the anode. At the cathode, atmospheric oxygen is reduced. The overall reaction is the oxidation of ethanol to acetic acid and water, which produces an electric current that may be detected and quantified by a microcontroller. A modified breathalyzer instrument exploiting other reactions may be used to detect various volatile organic compounds.

Figure 6:
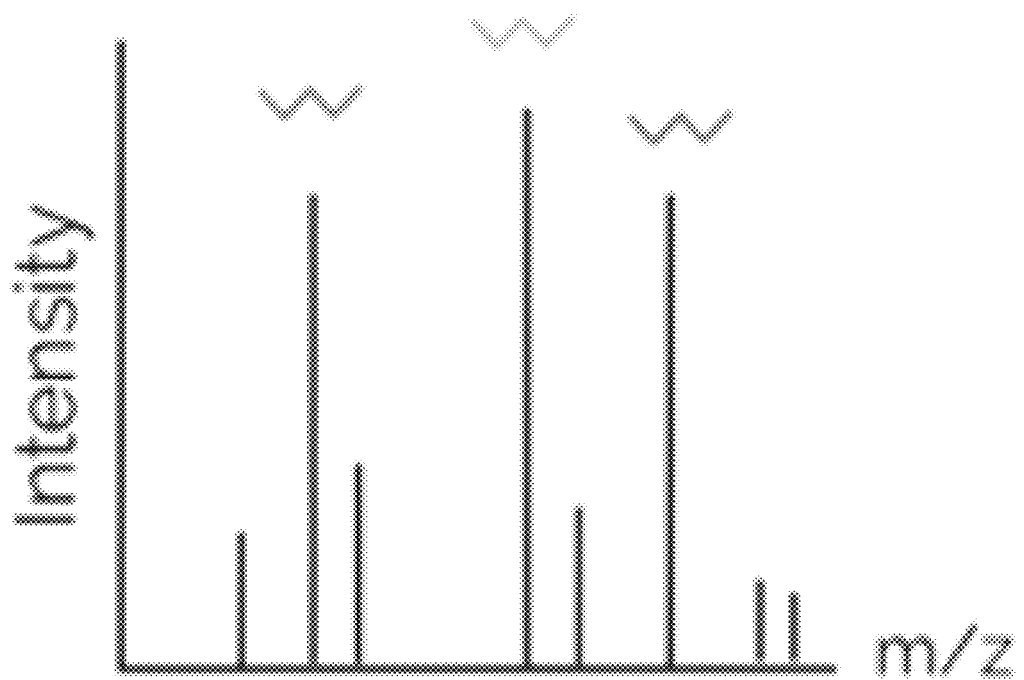
FIG. 6 shows activity detection according to certain embodiments.

FIG. 6 is a mass spectrum that may be used to detect a target activity, as described in step 125. Mass spectrometry may be used to detect and distinguish reporters based on differences in mass. In mass spectrometry, a sample is ionized, for example by bombarding it with electrons. The sample may be solid, liquid, or gas. By ionizing the sample, some of the sample's molecules are broken into charged fragments. These ions may then be separated according to their mass-to-charge ratio. This is often performed by accelerating the ions and subjecting them to an electric or magnetic field, where ions having the same mass-to-charge ratio will undergo the same amount of deflection. When deflected, the ions may be detected by a mechanism capable of detecting charged particles, for example, an electron multiplier. The detected results may be displayed as a spectrum of the relative abundance of detected ions as a function of the mass-to-charge ratio. The molecules in the sample can then be identified by correlating known masses, such as the mass of an entire molecule to the identified masses or through a characteristic fragmentation pattern.

When the reporter includes a nucleic acid, the reporter may be detected by various sequencing methods known in the art, for example, traditional Sanger sequencing methods or by next-generation sequencing (NGS). NGS generally refers to non-Sanger-based high throughput nucleic acid sequencing technologies, in which many (i.e., thousands, millions, or billions) of nucleic acid strands can be sequenced in parallel. Examples of such NGS sequencing includes platforms produced by Illumina (e.g., HiSeq, MiSeq, NextSeq, MiniSeq, and iSeq 100), Pacific Biosciences (e.g., Sequel and RSII), and Ion Torrent by ThermoFisher (e.g., Ion S5, Ion Proton, Ion PGM, and Ion Chef systems). It is understood that any suitable NGS sequencing platform may be used for NGS to detect nucleic acid of the detectable analyte as described herein.

Analysis may be performed directly on the biological sample or the detectable analyte may be purified to some degree first. For example, a purification step may involve isolating the detectable analyte from other components in the biological sample. Purification may include methods such as affinity chromatography. The isolated or purified detectable analyte does not need to be 100% pure or even substantially pure prior to analysis.

Detecting the detectable analyte may provide a qualitative assessment (e.g., whether the detectable analyte is present or absent) or a quantitative assessment (e.g., the amount of the detectable analyte present) to indicate a comparative activity level of the enzymes. The quantitative value may be calculated by any means, such as, by determining the percent relative amount of each fraction present in the sample. Methods for making these types of calculations are known in the art.

The detectable analyte may be labeled. For example, a label may be added directly to a nucleic acid when the isolated detectable analyte is subjected to PCR. For example, a PCR reaction performed using labeled primers or labeled nucleotides will produce a labeled product. Labeled nucleotides, such as fluorescein-labeled CTP are commercially available. Methods for attaching labels to nucleic acids are well known to those of ordinary skill in the art and, in addition to the PCR method, include, for example, nick translation and end-labeling.

Labels suitable for use in the reporter include any type of label detectable by standard methods, including spectroscopic, photochemical, biochemical, electrical, optical, or chemical methods. The label may be a fluorescent label. A fluorescent label is a compound including at least one fluorophore. Commercially available fluorescent labels include, for example, fluorescein phosphoramidides, rhodamine, polymethadine dye derivative, phosphores, Texas red, green fluorescent protein, CY3, and CY5.

Other known techniques, such as chemiluminescence or colormetric (enzymatic color reaction), can also be used to detect the reporter. Quencher compositions in which a "donor" fluorophore is joined to an "acceptor" chromophore by a short bridge that is the binding site for the enzyme may also be used. The signal of the donor fluorophore is quenched by the acceptor chromophore through a process believed to involve resonance energy transfer (RET), such as fluorescence resonance energy transfer (FRET). Cleavage of the peptide results in separation of the chromophore and fluorophore, removal of the quench, and generation of a subsequent signal measured from the donor fluorophore. Examples of FRET pairs include 5-Carboxyfluorescein (5-FAM) and CPQ2, FAM and DABCYL, Cy5 and QSY21, Cy3 and QSY7.

Figure 7:
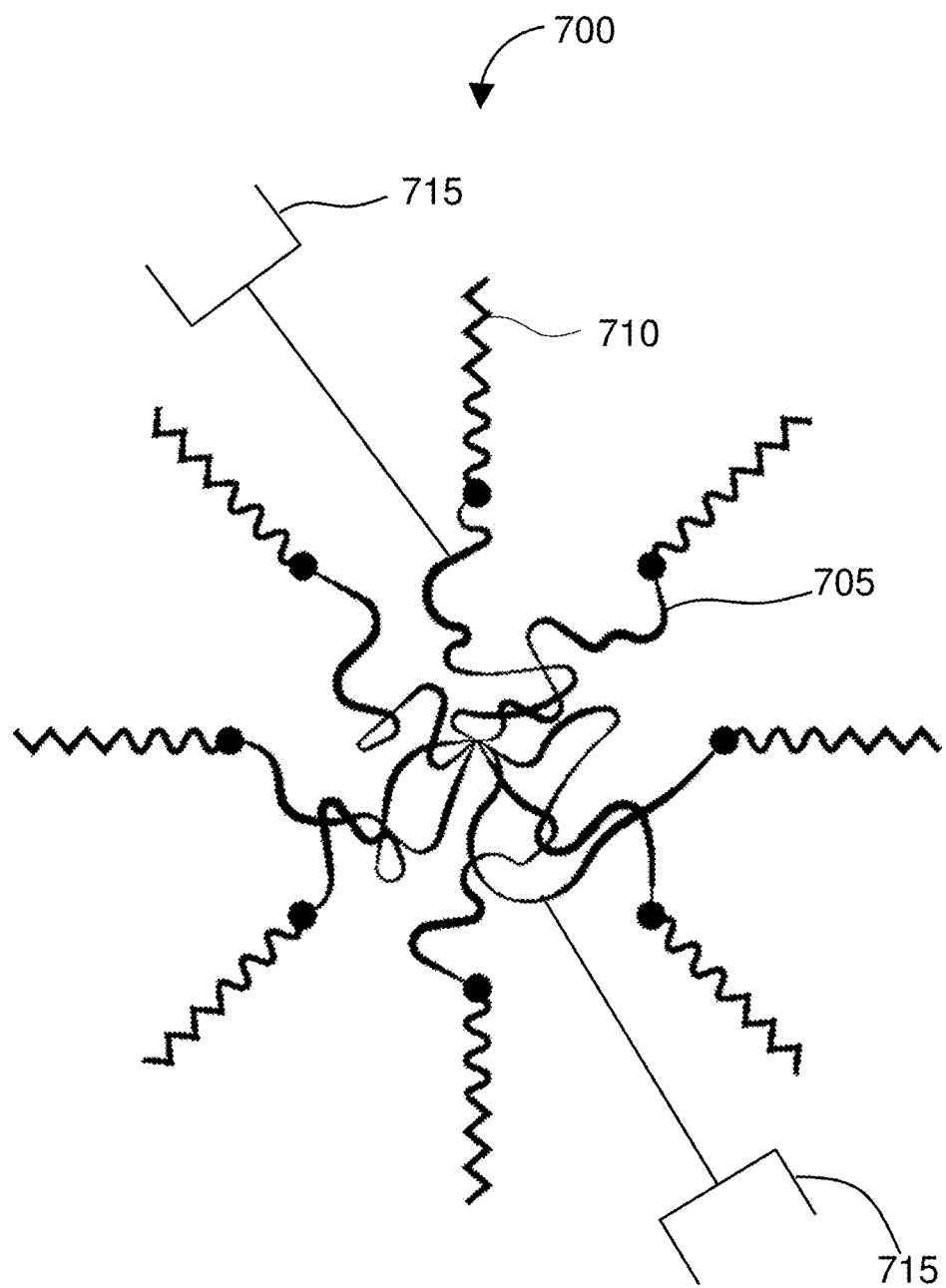
FIG. 7 shows an activity sensor with ligands for a specific cell or tissue type.

FIG. 7 shows an activity sensor 700 with ligands 715 for receptors of a specific cell or a specific tissue type as the tuning domains.

When administered to a subject, activity sensor 700 is trafficked in the body through various pathways depending on how it enters the body. For example, if activity sensor 700 is administered intravenously, it will enter systemic circulation from the point of injection and may be passively trafficked through the body.

For the activity sensor 700 to detect an enzymatic activity within a specific cell, at some point during its residence time in the body, activity sensor 700 must come into the presence of the enzyme and have an opportunity for the polypeptide reporter 710 to be cleaved by the enzyme. From a targeting perspective, it is advantageous to provide the activity sensor with a means to target specific cells or a specific tissue type where such enzymes of interest may be present. To achieve this, ligands 715 for receptors of the specific cell or specific tissue type may be provided as the tuning domains and linked to polypeptide 710.

Cell surface receptors are membrane-anchored proteins that bind ligands on the outside surface of the cell. In one example, the ligand may bind ligand-gated ion channels, which are ion channels that open in response to the binding of a ligand. The ligand-gated ion channel spans the cell's membrane and has a hydrophilic channel in the middle. In response to a ligand binding to the extracellular region of the channel, the protein's structure changes in such a way that certain particles or ions may pass through. By providing the activity sensor with tuning domains that include ligands for proteins present on the cell surface, the activity sensor has a greater opportunity to reach and enter specific cells to detect enzymatic activity within those cells.

Activity sensor 700 includes a biocompatible scaffold 705 as the carrier, polypeptides 710 as the reporters, and ligands 715 as the tuning domains.

As illustrated, carrier 705 is an 8-arm PEG-MAL scaffold, where the terminal end of each arm is linked to a reporter 710, and ligands 715 bind receptors of a specific cell or a specific tissue type. By providing the activity sensor 700 with tuning domains 715, distribution of the activity sensor 700 may be modified because ligands 715 may target the activity sensor to specific cells or specific tissues in a subject via binding of the ligand 715 to cell surface proteins on the targeted cells. The ligands of tuning domains 715 may be selected from a group including a small molecule; a peptide; an antibody; a fragment of an antibody; a nucleic acid; and an aptamer. For example, the ligand may include peptides conjugated to the scaffold of carrier 705 via maleimide-thiol coupling or amide bonds.

Once activity sensor 700 reaches the specific tissue, ligands 715 may also promote accumulation of the activity sensor in the specific tissue type. Accumulating the activity sensor 700 in the specific tissue increases the residence time of the activity sensor and provides a greater opportunity for the polypeptide reporter 710 to be enzymatically cleaved by proteases in the tissue, if such proteases are present.

Figure 8:
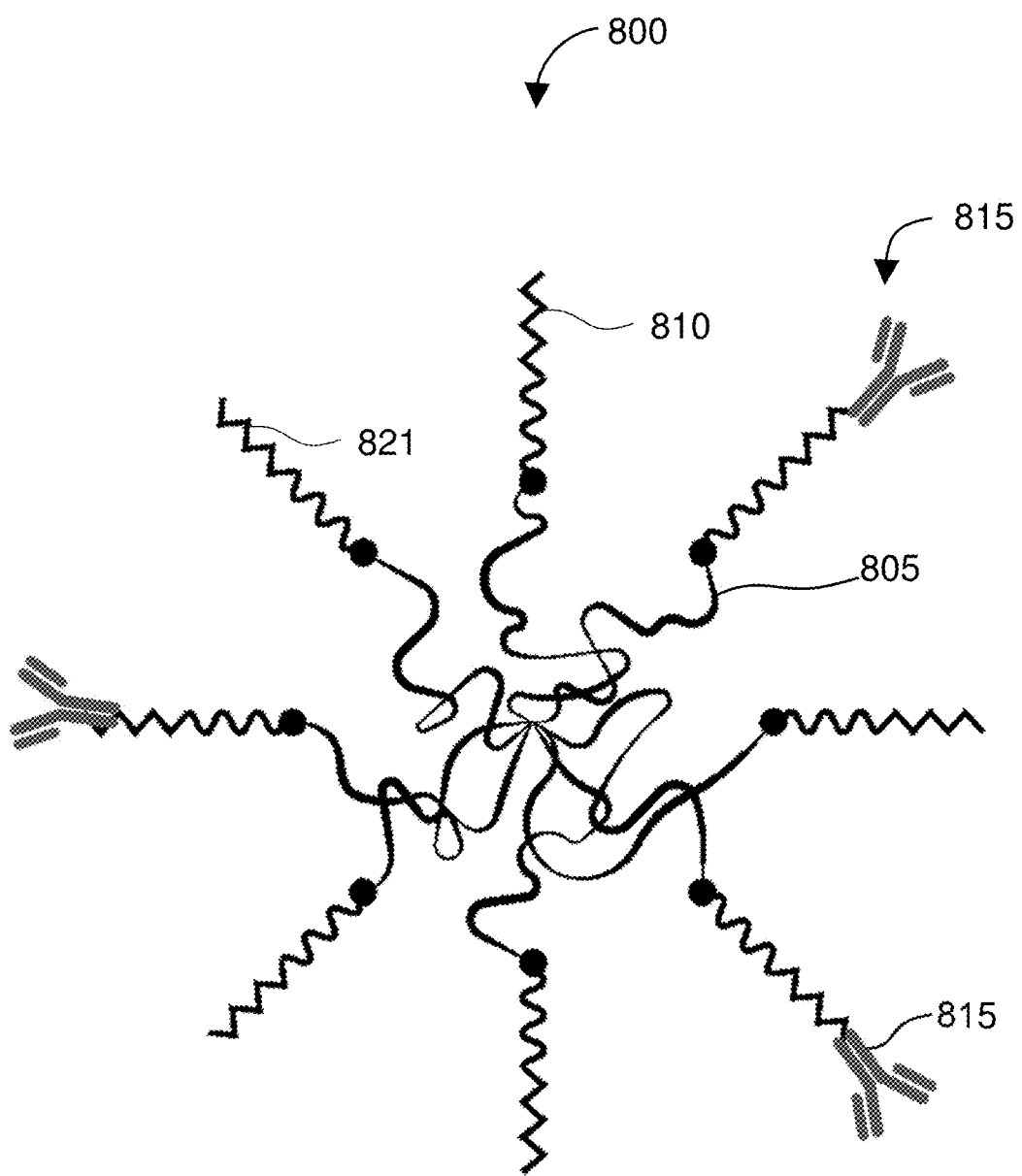
FIG. 8 shows an activity sensor with a biocompatible scaffold and tuning domains.

FIG. 8 shows an activity sensor 800 with a biocompatible scaffold 805 as the carrier and tuning domains 815 that promote accumulation of the activity sensor 800 in a specific tissue.

When the activity sensor 800 is administered to a subject, it may be recognized as a foreign substance by the immune system and subjected to immune clearance, thereby never reaching the specific cells or specific tissue where reporters 810 may detect enzymatic activity. To inhibit immune detection, it is preferable to use a biocompatible scaffold 805 as the carrier so that it does not elicit an immune response, for example, a biocompatible scaffold that includes multiple subunits of covalently linked poly(ethylene glycol) maleimide. Further, the molecular weight of the poly(ethylene glycol) maleimide scaffold may be modified to facilitate trafficking within the body and to prevent clearance of the activity sensor by the reticuloendothelial system. Through such modifications, the distribution and residence time of the activity sensor in the body or in specific tissues may be improved.

Activity sensor 800 includes a carrier 805 that is a biocompatible scaffold, and a polypeptide reporter 810 and antibodies 815 as tuning domains.

As illustrated, carrier includes multiple subunits of covalently linked poly(ethylene glycol) maleimide to form an 8-arm PEG-MAL scaffold 805. This PEG-MAL scaffold 805 has a molecular weight between about 20 and 80 kDa. Polypeptides 821 are linked to the terminal ends of each of the eight arms of the scaffold 805. Antibodies 815 are provided as tuning domains to promote accumulation of the activity sensor 800 in a specific tissue where antigens of antibodies 815 are present. By providing the activity sensor 800 with antibodies 815, distribution of the activity sensor 800 may be modified binding of antibodies 815 to cell surface proteins on cells of specific tissues that are recognized as antigens.

In certain embodiments, tuning domains 815 may be selected from a group including a small molecule; a peptide; an antibody; a fragment of an antibody; a nucleic acid; and an aptamer.

Figure 9:
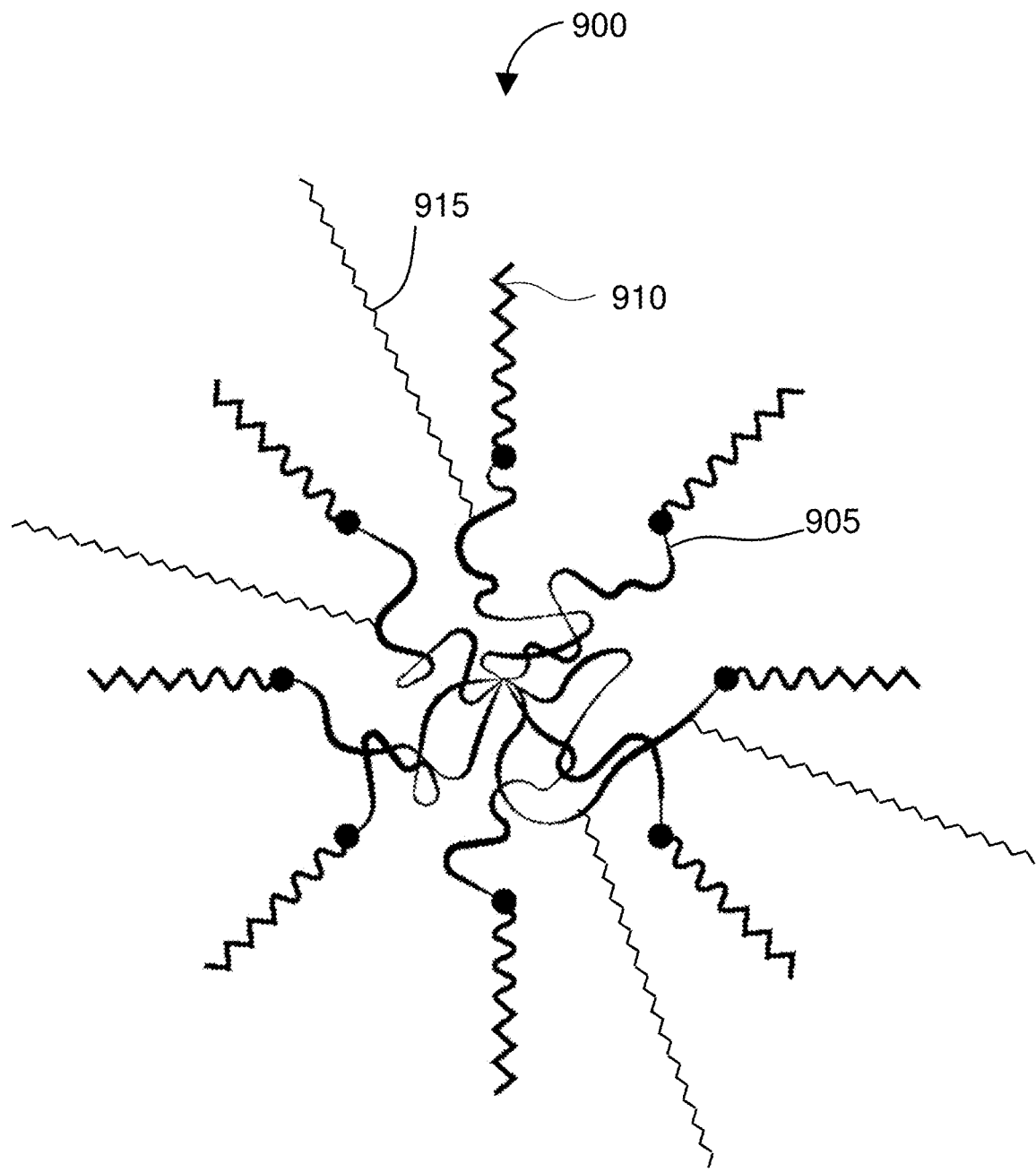
FIG. 9 shows an activity sensor with hydrophobic chains.

FIG. 9 shows an activity sensor 900 with hydrophobic chains 915 provided as tuning domains to facilitate diffusion of the activity sensor across a cell membrane.

When administered to a subject, the activity sensor 900 is trafficked in the body through various pathways depending on how it enters the body. For example, if the activity sensor 900 is administered intravenously, it will enter systemic circulation from the point of injection and may be passively trafficked through the body.

For the activity sensor 900 to detect an enzymatic activity within a specific cell, at some point during its residence time in the body, the activity sensor 900 must come into the presence of the enzyme and have an opportunity for reporter 910 to be cleaved by the enzyme. Therefore, it is advantageous to provide the activity sensor with a means to enter specific cells where such enzymes of interest may be present. To achieve this, hydrophobic chains 915 are provided as tuning domains to facilitate diffusion of the activity sensor across a cell membrane may be linked to the activity sensor 900.

Activity sensor 900 includes a carrier 905, a reporter 910 that is linked to the carrier, and tuning domains 915 that include hydrophobic chains.

As illustrated, 8-arm PEG-MAL scaffold 905 is the carrier, where the terminal end of each arm is linked to a reporter 910, and the fatty acid chains 915 are provided as tuning domains to facilitate diffusion of the activity sensor 900 across lipid cell membranes.

The tuning domains may include any suitable hydrophobic chains that facilitate diffusion, for example, fatty acid chains including neutral, saturated, (poly/mono) unsaturated fats and oils (monoglycerides, diglycerides, triglycerides), phospholipids, sterols (steroid alcohols), zoosterols (cholesterol), waxes, and fat-soluble vitamins (vitamins A, D, E, and K).

In some embodiments, the tuning domains include cell-penetrating peptides. Cell-penetrating peptides (CPPs) are short peptides that facilitate cellular intake/uptake of activity sensors of the disclosure. CPPs preferably have an amino acid composition that either contains a high relative abundance of positively charged amino acids such as lysine or arginine or has sequences that contain an alternating pattern of polar/charged amino acids and non-polar, hydrophobic amino acids. See Milletti, 2012, Cell-penetrating peptides: classes, origin, and current landscape, Drug Discov Today 17:850-860, incorporated by reference. Suitable CPPs include those known in the literature as Tat, R6, R8, R9, Penetratin, pVEc, RRL helix, Shuffle, and Penetramax. See Kristensen, 2016, Cell-penetrating peptides as tools to enhance non-injectable delivery of biopharmaceuticals, Tissue Barriers 4(2):e1178369, incorporated by reference.

Figure 10:
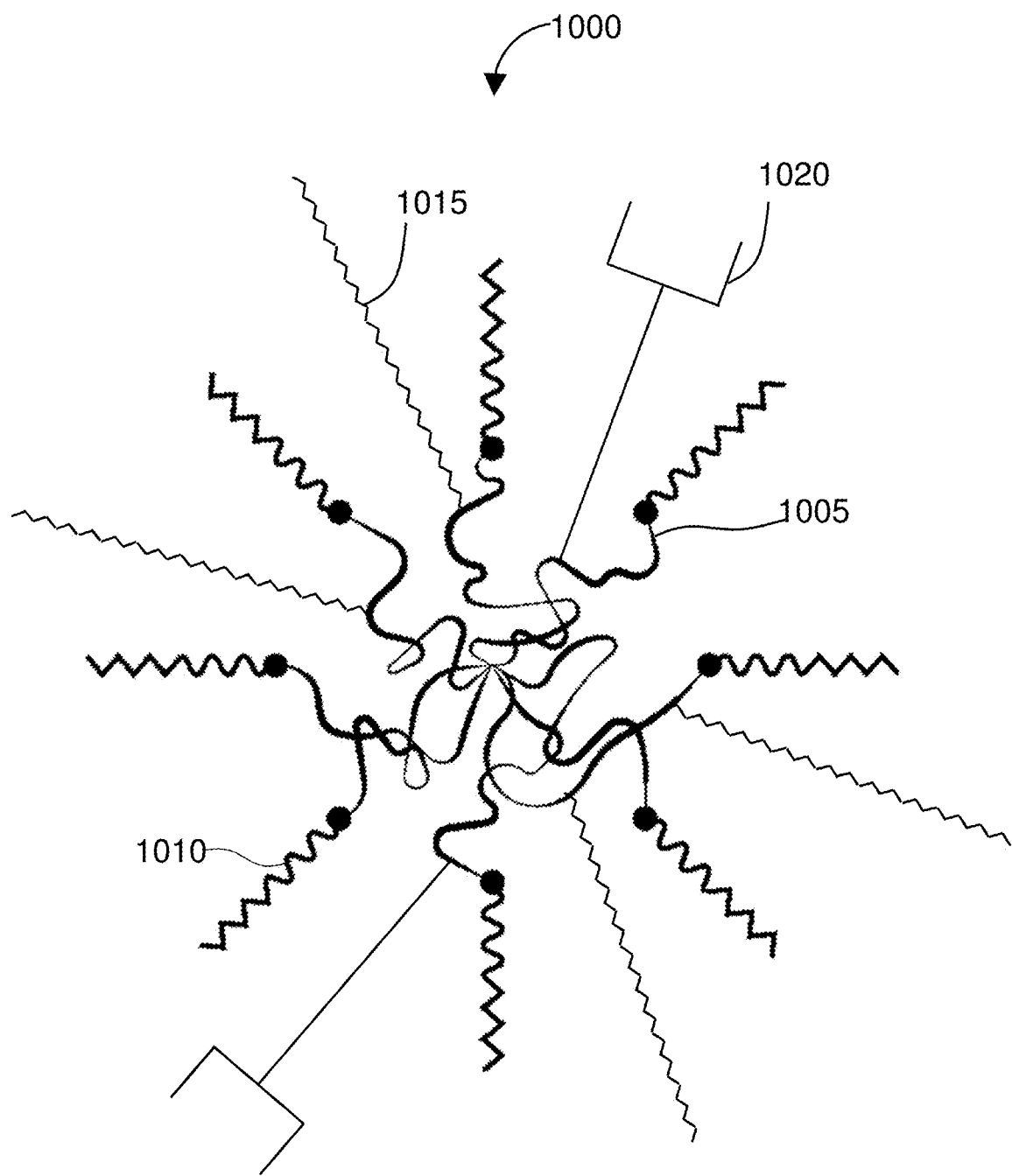
FIG. 10 shows an activity sensor with ligands for cell receptors.

FIG. 10 shows an activity sensor 1000 with peptide ligands 1020 for receptors of a specific cell or tissue type as tuning domains, and hydrophobic chains 1015 that facilitate diffusion of the activity sensor 1000 across a cell membrane.

When administered to a subject, the activity sensor 1000 is trafficked in the body through various pathways depending on how it enters the body. For example, if the activity sensor 1000 is administered intravenously, it will enter systemic circulation from the point of injection and may be passively trafficked through the body.

For the activity sensor 1000 to detect an enzymatic activity within a specific cell, at some point during its residence time in the body, the activity sensor 1000 must come into the presence of the enzyme and have an opportunity for the reporter 1005 to be cleaved by the enzyme. Therefore, it is advantageous to provide the activity sensor with a means to target specific cells to detect enzymatic activity within those cells. To achieve this, peptide ligands 1015 for receptors of a specific cell or tissue type are provided as tuning domains and linked to the reporters 1010. In addition, it is advantageous to provide the activity sensor 1000 with a means to enter those specific cells where such enzymes of interest may be present. To achieve this, hydrophobic chains 1015 are linked to activity sensor 1000 to facilitate diffusion of activity sensor 1000 across cell membranes.

Cell surface receptors are membrane-anchored proteins that bind ligands on the surface of the cell. In one example, the ligand can bind ligand-gated ion channels, which are ion channels that open in response to the binding of a ligand. The ligand-gated ion channel spans the cell's membrane and has a hydrophilic channel in the middle. In response to a ligand binding to the extracellular region of the channel, the protein's structure changes in such a way that certain particles or ions may pass through. By providing the activity sensor with tuning domains that include ligands for proteins present on the cell surface, the activity sensor has a greater opportunity to reach and enter specific cells to detect enzymatic activity within those cells.

Activity sensor 1000 includes carrier 1005, a reporter 1010 that is linked to the carrier, and tuning domains 1015 and tuning domains 1020.

As illustrated, carrier 1005 is an 8-arm PEG-MAL scaffold, where the terminal end of each arm is linked to a reporter 1010, and the tuning domains 1015 include peptide ligands for receptors of a specific cell or tissue type, and hydrophobic chains 1020 that facilitate diffusion of the activity sensor across a cell membrane. By linking tuning domains 1015 to activity sensor 1000, the activity sensor 1000 may be targeted to a specific cell or tissue type and the hydrophobic chains allow the activity sensor 1000 to diffuse through the lipid bilayer of the cellular membrane to enter the cell. After entering the cell, if enzymes able to cleave the reporter 1010 from the carrier are present, those enzymes may cleave and liberate the reporter 1010 from the activity sensor 1000. The reporter 1010 may then be excreted from the body and detected to determine a disease state, or disease progression or regression.

The tuning domains may include any suitable hydrophobic chains that facilitate diffusion, for example, fatty acid chains including neutral, saturated, (poly/mono) unsaturated fats and oils (monoglycerides, diglycerides, triglycerides), phospholipids, sterols (steroid alcohols), zoosterols (cholesterol), waxes, and fat-soluble vitamins (vitamins A, D, E, and K).

Figure 11:
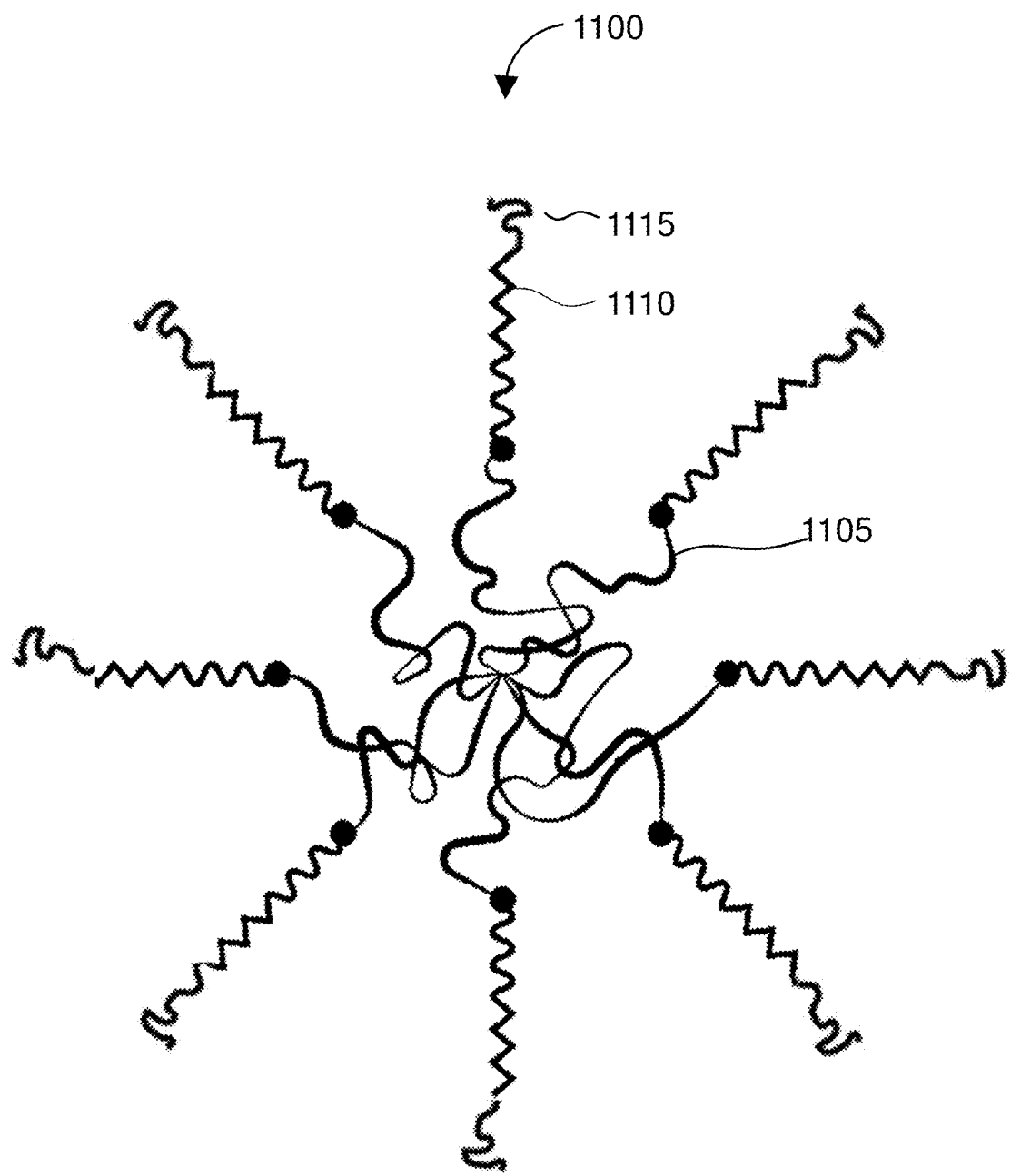
FIG. 11 shows an activity sensor with biocompatible polymers.
Figure 12:
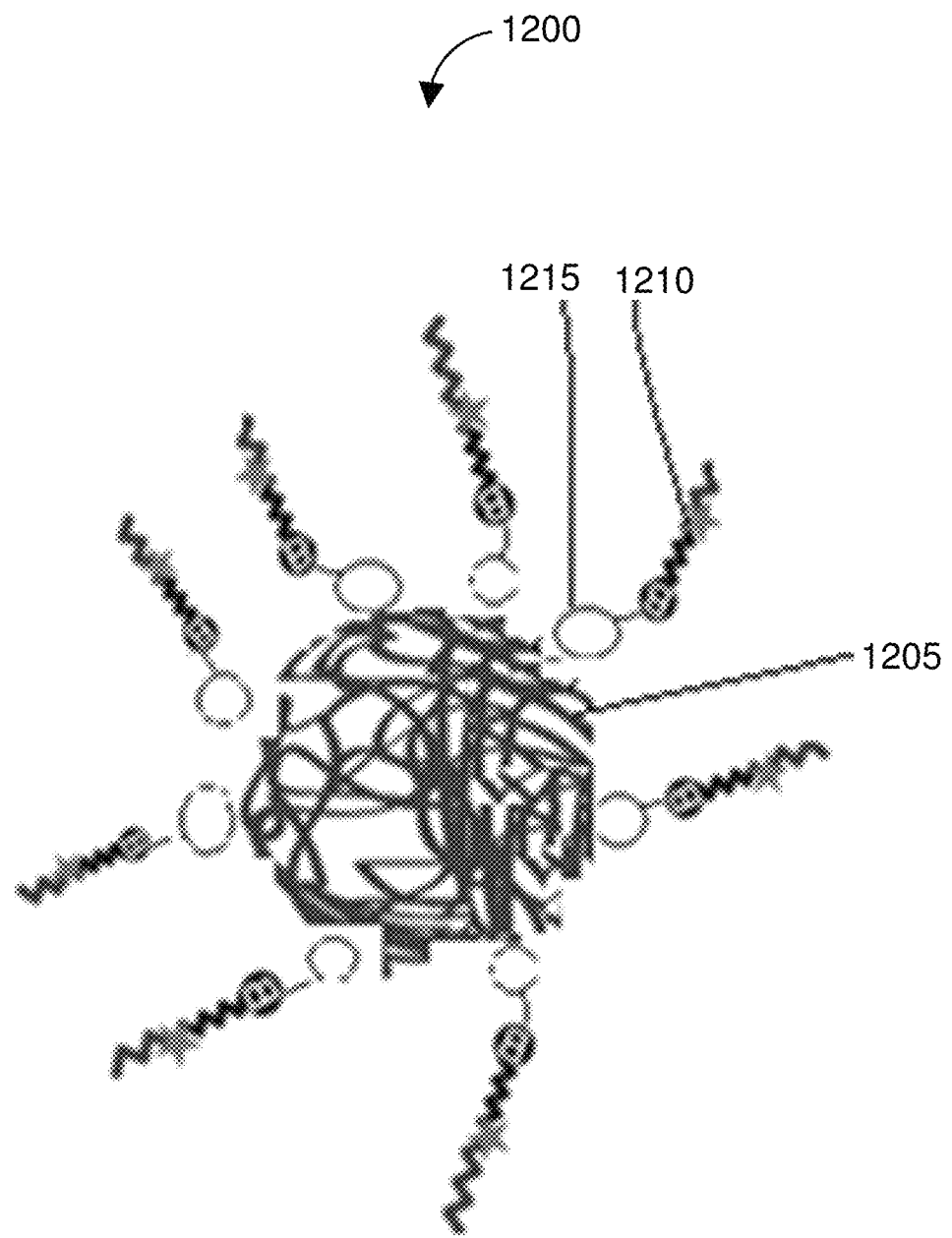
FIG. 12 shows an activity sensor with polymers between the carrier and reporter.
Figure 13:
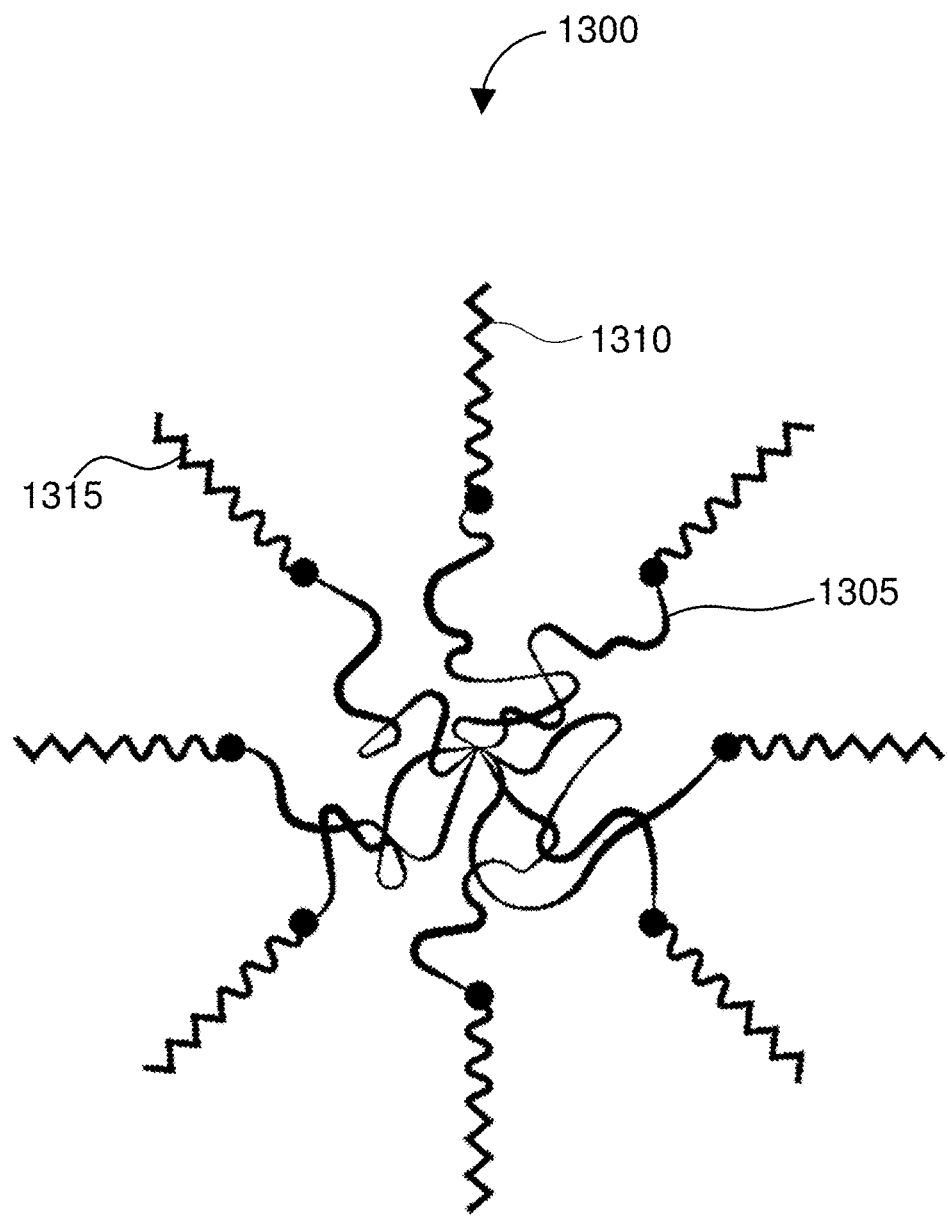
FIG. 13 shows an activity sensor with tuning domains with D-amino acids.

FIG. 11 shows an activity sensor 1100 with biocompatible polymer 1115 as the tuning domains to shield the polypeptides reporters 1110 from immune detection or inhibit cellular uptake of the activity sensor 1100 by macrophages.

When administered to a subject, the activity sensor 1100 is trafficked in the body through various pathways depending on how it enters the body. For example, if the activity sensor 1100 is administered intravenously, it will enter systemic circulation from the point of injection and may be passively trafficked through the body.

For the activity sensor 1100 to detect an enzymatic activity within a specific cell, at some point during its residence time in the body, the activity sensor 1100 must come into the presence of the enzyme and have an opportunity for the reporter 1110 to be cleaved by the enzyme.

When a foreign substance is recognized as an antigen, an antibody response may be triggered by the immune system. Generally, antibodies will then attach to the foreign substance, forming antigen-antibody complexes, which are then ingested by macrophages and other phagocytic cells to clear those foreign substances from the body. As such, when activity sensor 1100 enters the body, it may be recognized as an antigen and subjected to immune clearance, preventing the activity sensor 1100 from reaching a specific tissue to detect enzymatic activity. To inhibit immune detection of the activity sensor 1110, for example, PEG tuning domains 1115 may be linked to the activity sensor 1100. PEG acts as a shield, inhibiting recognition of the activity sensor 1100 as a foreign substance by the immune system. By inhibiting immune detection, the tuning domains 1115 improve the residence time of the activity sensor 1100 in the body or in a specific tissue.

Macrophages are a type of white blood cell of the immune system that engulfs and digests things that lack certain cell surface proteins that are characteristic of healthy body cells. For example, macrophages can engulf and digest foreign substances, microbes, cellular debris, cancer cells. Macrophages may be found in essentially all tissues of the body and provide a form of nonspecific defense.

When the activity sensor 1100 enters the body, it may be recognized as a foreign substance and macrophages may engulf and digest it, preventing the activity sensor 1100 from reaching specific tissues. To inhibit cellular uptake of the activity sensor 1100 by macrophages, for example, PEG 1115 may be linked to the activity sensor 1100. PEG 1115 acts as a shield, inhibiting recognition of the activity sensor as a foreign substance by macrophages. By inhibiting macrophage recognition, the tuning domains 1115 improve the residence time of the activity sensor 1100 in the body or in a specific tissue, allowing activity sensor 1100 to reach specific tissues to detect enzymatic activity.

Activity sensor 1100 includes a carrier 1105 that is a bio-compatible scaffold and polypeptide reporters 1110 each linked to carrier 1105. Polypeptides 1110 are susceptible to cleavage by one or more proteases. Activity sensor 1100 also includes a plurality of polymer tuning domains 1115 that shield polypeptides 1110 from immune detection or inhibit cellular uptake of the activity sensor by macrophages. Polypeptides 1110 may include sequences susceptible to cleavage by proteases known to be associated with a specific disease and the tuning domain polymers may include PEG side chains. Reporter 1110 may include any polypeptide susceptible to enzymatic cleavage.

As illustrated, carrier 1105 is an 8-arm PEG-MAL scaffold, where the terminal end of each arm is linked to polypeptides 1110. Activity sensor 1100 includes tuning domains 1115 linked to polypeptides 1110 to shield polypeptides 1110 from immune detection, which prevents immune clearance of activity sensor 1100 prior to reaching a specific tissue. Similarly, the PEG 1115 inhibits recognition of activity sensor 1100 by macrophages. When macrophages are unable to recognize activity sensor 1100, activity sensor 1100 is protected from cellular uptake and premature degradation. In either event of shielding activity sensor 1100 from immune detection or inhibiting cellular uptake of the activity sensor by macrophages, the tuning domains 1115 improve the residence time of the activity sensor 1100 in the subject, thereby allowing it to reach a specific tissue and detect enzymatic activity.

FIG. 12 shows an activity sensor 1200 with polymers 1215 as tuning domains, where polymers 1215 are positioned between the carrier scaffold 1205 and polypeptides reporters 1210 to decrease steric hindrance between scaffold 1205 and polypeptides reporters 1210, thereby increasing accessibility of polypeptides 1210 to proteases and promoting successful cleavage.

When administered to a subject, activity sensor 1200 is trafficked in the body through various pathways depending on how it enters the body. For example, if activity sensor 1200 is administered intravenously, it will enter systemic circulation from the point of injection and may be passively trafficked through the body.

For activity sensor 1200 to detect an enzymatic activity within a specific cell, at some point during its residence time in the body, activity sensor 1200 must come into the presence of the enzyme and have an opportunity for the reporter to be cleaved by the enzyme. Enzymes have a high specificity for specific substrates by binding pockets with complementary shape, charge and hydrophilic/hydrophobic characteristic of the substrates. As such, enzymes can distinguish between very similar substrate molecules to be chemoselective (i.e., preferring an outcome of a chemical reaction over an alternative reaction), regioselective (i.e., preferring one direction of chemical bond making or breaking over all other possible directions), and stereospecific (i.e., only reacting on one or a subset of stereoisomers).

Steric effects are nonbonding interactions that influence the shape (i.e., conformation) and reactivity of ions and molecules, which results in steric hindrance. Steric hindrance is the slowing of chemical reactions due to steric bulk, affecting intermolecular reactions. Various groups of a molecule may be modified to control the steric hindrance among the groups, for example to control selectivity, such as for inhibiting undesired side-reactions. By providing the activity sensor with tuning domains between the carrier scaffold and the reporters, steric hindrance among components of activity sensor 1200 may be minimized to increase accessibility of the reporters to proteases.

To detect a target activity, polypeptides 1210 must be cleaved, liberating a portion of polypeptides 1210 from scaffold 1205. To promote successful cleavage, polymers 1215 may be linked to scaffold 1205 and polypeptides 1210, between scaffold 1205 and polypeptides 1210. By decreasing steric hindrance between scaffold 1205 and polypeptides 1210, polypeptides 1210 may be presented to enzymes to allow the enzymes to cleave polypeptides 1210. In certain embodiments, polymers 1215 may be PEG or any other suitable biocompatible polymer.

In one embodiment, activity sensor 1200 includes a bio-compatible scaffold carrier 1205 that is about 30 to 40 kDa, and polypeptide reporters 1210 each linked to scaffold 1205. Activity sensor 1200 also includes polymer tuning domains 1215 positioned between scaffold 1205 and polypeptides 1210 to decrease steric hindrance between scaffold 1205 and polypeptides 1210, thereby increasing accessibility of polypeptides 1210 to proteases and promoting successful cleavage.

As illustrated, carrier 1205 is an 8-arm PEG-MAL scaffold, where the terminal end of each arm is linked to PEG 1215 positioned between scaffold 1205 and polypeptides 1210 to decrease steric hindrance between scaffold 1205 and polypeptides 1210. By decreasing steric hindrance among parts of activity sensor 1200, PEG 1215 increases accessibility of polypeptides 1210 to the proteases to promote successful cleavage.

Polymers 1215 may be of any size and may be selected to adjust the distance between scaffold 1205 and polypeptides 1210 In some embodiments, the distance between scaffold 1205 and polypeptides 1210 ranges from about 1.5 angstroms to about 1000 angstroms, about 10 angstroms to about 500 angstroms (e.g., any integer between 10 and 500), about 50 angstroms to about 800 angstroms (e.g., any integer between 50 and 800), about 600 angstroms to about 1000 angstroms (e.g., any integer between 600 and 1000), or greater than 1000 angstroms.

Polymers 1215 may include synthetic polymers such as polymers of lactic acid and glycolic acid, polyanhydrides, polyurethanes, or natural polymers such as alginate and other polysaccharides including dextran and cellulose, collagen, albumin and other hydrophilic proteins, zein and other prolamines and hydrophobic proteins, copolymers and mixtures thereof.

FIG. 13 shows an activity sensor 1300 with a polypeptide reporters 1310 and tuning domains 1315 that compose regions of polypeptides 1310 that include D-amino acids to prevent proteolytic cleavage of those regions.

Enzymes can distinguish between very similar substrate molecules because enzymes are chemoselective (i.e., preferring an outcome of a chemical reaction over an alternative reaction), regioselective (i.e., preferring one direction of chemical bond making or breaking over all other possible directions), and stereospecific (i.e., only reacting on one or a subset of stereoisomers). Amino acids may occur as either L- or D-amino acids. L- and D-amino acids generally refer to the left-handed and right-handed configurations of an amino acid, respectively, and represent two different enantiomers (stereoisomers) around the central carbon atom.

Generally, only L-amino acids are manufactured in cells; D-amino acids are not. Because enzymes are stereospecific, most proteases are unable to cleave a peptide chain at positions containing D-amino acids. As such, by providing tuning domains 1315 as regions of the polypeptide 1310, where tuning domains 1315 include D-amino acids, the tuning domains 1315 prevent proteolytic cleavage of such regions.

In addition, a cleavage site of the polypeptides in tissue of a specific type may be determined by a composition or relative order of the L- and D-amino acids in the polypeptides. By modifying the relative order or composition of the amino acids in the reporter as well as the tuning domain, a site of cleavage may be controlled by only providing L-amino acids at the intended cleavage site, and D-amino acids in other regions to be protected. Also, peptides composed of D-amino acids are resistant to endogenous peptidases and proteases, and are less likely to induce a humoral immune response in a subject.

Though illustrated with D-amino acids, other non-natural amino acids may be incorporated into the polypeptides of the plurality of tuning domains 1315, including synthetic non-native amino acids, substituted amino acids, or one or more D-amino acids.

Activity sensor 1300 includes a bio-compatible scaffold 1305 as the carrier, polypeptides 1310 each linked to scaffold 1305, and tuning domains 1315 that include D-amino acids, where tuning domains 1315 compose regions of polypeptides 1310 to prevent proteolytic cleavage of those regions. In addition, where the proteases are known to be expressed with a certain disease or medical condition, and activity sensor 1300 is delivered to tissue of a subject affected by the disease or condition, those proteases may cleave polypeptide 1310 and release of an analyte detectable in a sample from the subject. In certain embodiments, the D-amino acids may protect the detectable analyte from digestion until detection.

As illustrated, an 8-arm PEG-MAL scaffold 1305 is provided as the carrier, where the terminal end of each arm is linked to each peptide chain 1310 as reporters. Tuning domains 1315 compose regions of polypeptides 1310. By providing activity sensor 1300 with tuning domains 1315, proteolytic cleavage of polypeptide 1310 may be controlled and proteolytic cleavage of regions including D-amino acids may be prevented.

Figure 14:
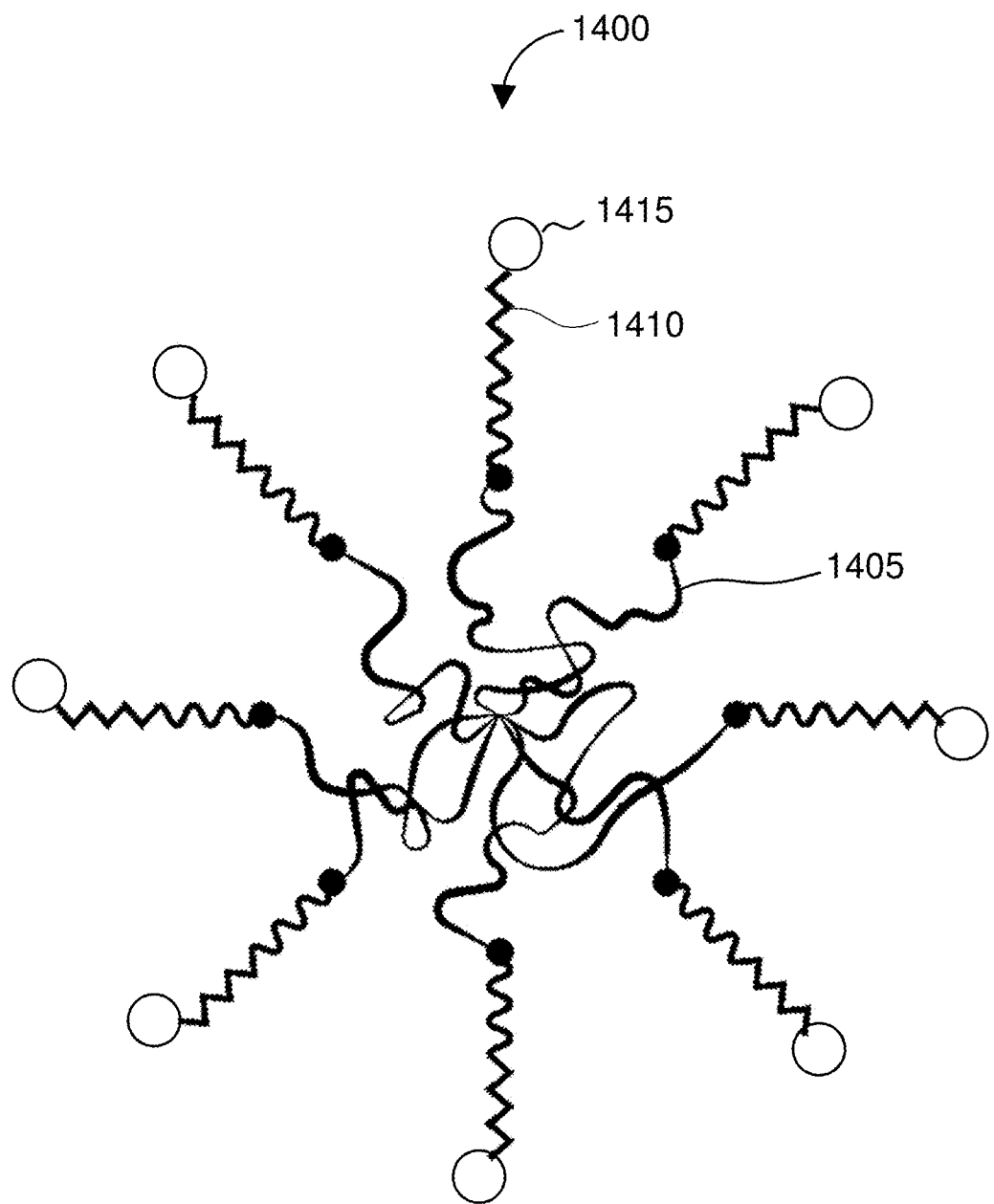
FIG. 14 shows an activity sensor with polymer tuning domains.

FIG. 14 shows an activity sensor 1400 with a polypeptide reporter 1410 and polymer tuning domains 1415 linked to reporter 1410 that facilitate passage of reporter 1410 into systemic circulation after cleavage.

When administered to a subject, activity sensor 1400 is trafficked in the body through various pathways depending on how it enters the body. For example, if activity sensor 1400 is administered intravenously, it will enter systemic circulation from the point of injection and may be passively trafficked through the body.

For activity sensor 1400 to detect an enzymatic activity within a specific cell, at some point during its residence time in the body, activity sensor 1400 must come into the presence of the enzyme and have an opportunity for reporter 1410 to be cleaved by the enzyme. Similarly, after reporter 1410 is cleaved, liberating reporter 1410 from carrier 1405, reporter 1410 preferably diffuses out of the tissue into systemic circulation to be excreted from the body for detection. To promote diffusion to systemic circulation, polymers 1415 may be linked to activity sensor 1400 to facilitate passage of reporters 1410 into systemic circulation after cleavage. For example, PEG tuning domains 1415 may be linked to reporter 1410. PEG acts as a shield, inhibiting recognition of reporter 1410 as a foreign substance by the immune system. By inhibiting immune detection, PEG 1415 facilitates diffusion of reporter 1410 to systemic circulation.

Activity sensor 1400 includes scaffold 1405 and reporters 1410 each linked to carrier 1405. Activity sensor 1400 also includes polymers 1415 as tuning domains to facilitate passage of reporters 1410 into systemic circulation after cleavage.

As illustrated, carrier 1405 is an 8-arm PEG-MAL scaffold, where the terminal end of each arm is linked to polypeptides 1410. Once polypeptides 1410 are cleaved from scaffold 1405, the cleaved portions of polypeptides 1410 may be detected as detectable analytes. These detectable analytes preferably return to systemic circulation from the tissue in order to pass renal filtration and be excreted in urine. PEG tuning domains 1415 may be linked to the detectable analyte to facilitate passage of the detectable analyte into systemic circulation after cleavage.

Polymers 1415 may include synthetic polymers such as polymers of lactic acid and glycolic acid, polyanhydrides, polyurethanes, and natural polymers such as alginate and other polysaccharides including dextran and cellulose, collagen, albumin and other hydrophilic proteins, zein and other prolamines and hydrophobic proteins, copolymers and mixtures thereof.

Figure 15:
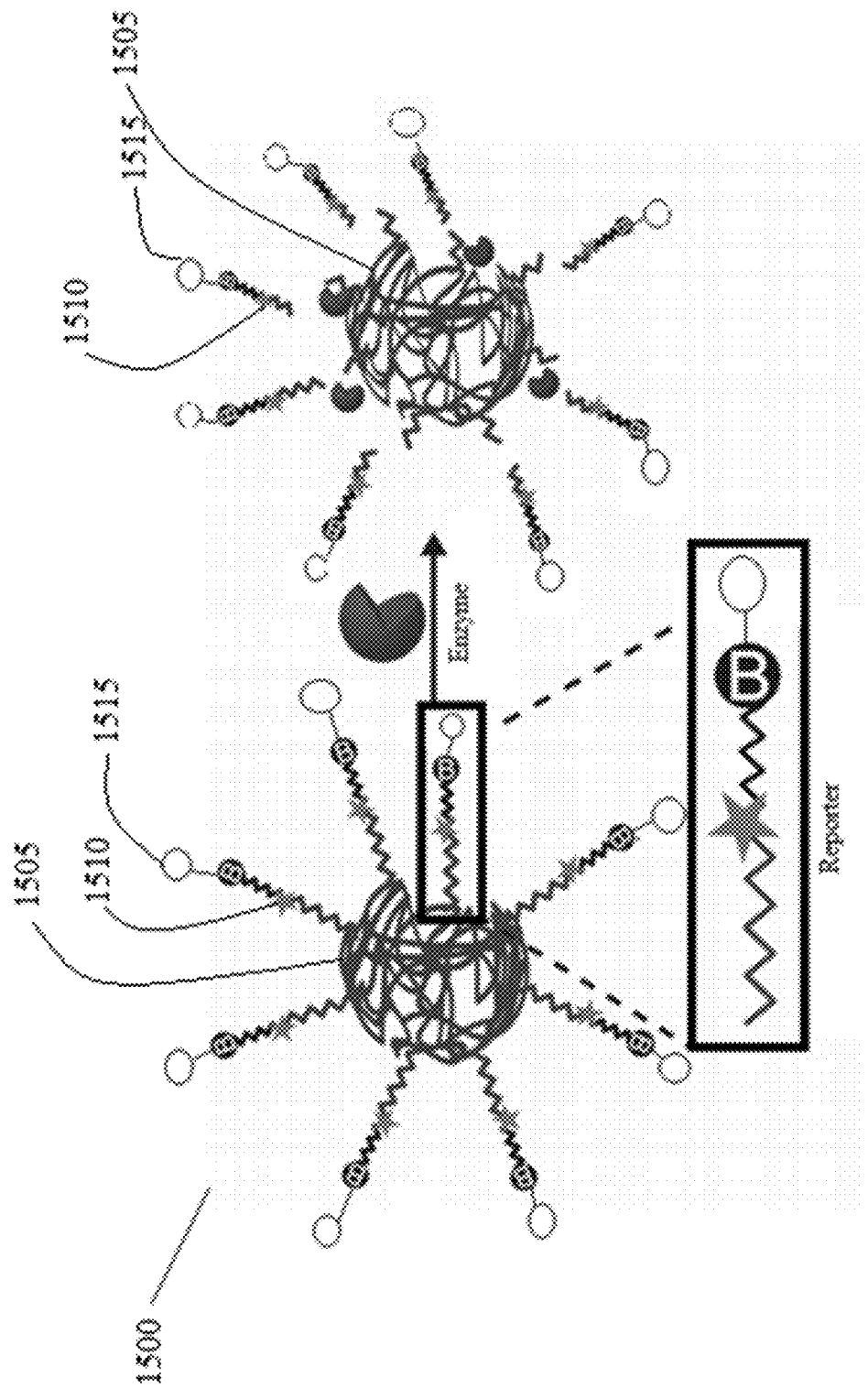
FIG. 15 shows an activity sensor with polymer tuning domains.

FIG. 15 shows an activity sensor 1500 with a polypeptide reporters 1510 and polymers 1515 as tuning domains to inhibit enzymatic activity upon a cleaved portion of polypeptides 1510, prior to excretion from the subject.

When administered to a subject, the activity sensor 1500 is trafficked in the body through various pathways depending on how it enters the body. For example, if activity sensor 1500 is administered intravenously, it will enter systemic circulation from the point of injection and may be passively trafficked through the body.

For activity sensor 1500 to detect an enzymatic activity within a specific cell, at some point during its residence time in the body, activity sensor 1500 must come into the presence of the enzyme and have an opportunity for polypeptides 1510 to be cleaved by the enzyme. Similarly, after polypeptides 1510 are cleaved to release a detectable analyte, the detectable analyte preferably diffuses out of the tissue into systemic circulation to be excreted from the body for detection. It is also important that the detectable analyte is not unintentionally cleaved by other enzymes. For example, if the selected detection method is by mass spectrometry, it is important that the detectable analyte stay substantially intact prior to excretion of the subject so that an accurate measurement of its mass may be determined.

To inhibit enzymatic activity upon the detectable analyte after cleavage, tuning domains 1515 may be linked to or coated on any part or all of reporter 1510, including the detectable analyte portion. For example, PEG tuning domains 1515 may be linked to or coated on any part or all of reporter 1510, including the detectable analyte portion. PEG acts as a shield, inhibiting enzymatic activity on polypeptides 1510 both before and after cleavage.

As illustrated, an 8-arm PEG-MAL scaffold 1505 is provided as the carrier, where the terminal end of each arm is linked to each polypeptide reporter 1510. Once polypeptides 1510 are cleaved, PEG tuning domains 1515 inhibit enzymatic activity upon the detectable analyte prior to excretion from the subject.

The polymers used in tuning domains 1515 may include synthetic polymers such as polymers of lactic acid and glycolic acid, polyanhydrides, polyurethanes, and natural polymers such as alginate and other polysaccharides including dextran and cellulose, collagen, albumin and other hydrophilic proteins, zein and other prolamines and hydrophobic proteins, copolymers and mixtures thereof.

Figure 16:
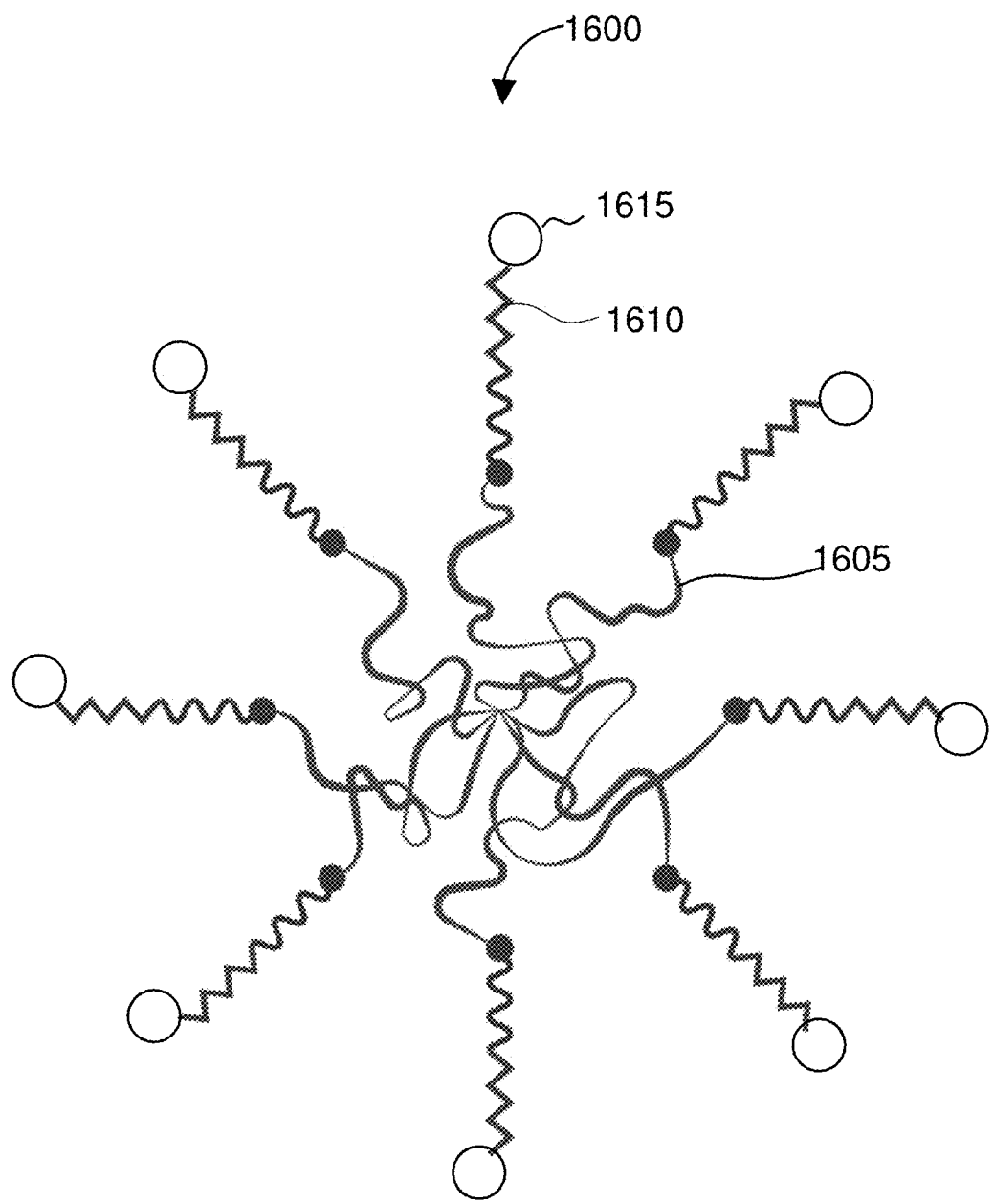
FIG. 16 shows an activity sensor with biocompatible polymer tuning domains.

FIG. 16 shows an activity sensor 1600 with biocompatible polymer tuning domains 1615 to protect activity sensor 1600 from immune detection and clearance.

When administered to a subject, activity sensor 1600 is trafficked in the body through various pathways depending on how it enters the body. For example, if activity sensor 1600 is administered intravenously, it will enter systemic circulation from the point of injection and may be passively trafficked through the body.

For activity sensor 1600 to detect an enzymatic activity within a specific cell, at some point during its residence time in the body, activity sensor 1600 must come into the presence of the enzyme and have an opportunity for reporters 1610 to be cleaved by the enzyme. While being trafficked through the body, it is preferable that activity sensor 1600 is not recognized as a foreign substance by the immune system and subjected to immune clearance, thereby never reaching the specific cells or specific tissue where reporters 1610 may detect enzymatic activity. To inhibit immune detection, biocompatible polymers 1615 may be linked to activity sensor 1600 to protect activity sensor 1600 from immune detection and clearance. For example, the tuning domains may include PEG, PVA, or a PVP polymer. PEG acts as a shield, inhibiting recognition of activity sensor 1600 as a foreign substance by the immune system. By inhibiting immune detection, tuning domains 1615 improve the residence time of activity sensor 1600 in the body or in a specific tissue and facilitate the desired distribution of activity sensor 1600 to the specific tissue.

As illustrated, an 8-arm PEG-MAL scaffold 1605 is provided as the carrier, where the terminal end of each arm is linked to reporters 1610. As shown, PEG tuning domains 1615 are linked to reporters 1610 to protect activity sensor 1600 from immune detection and clearance. PEG 1615 protects activity sensor 1600 from immune detection and clearance. In this example, the reporter 1610 is an elemental mass tag including an element of atomic number greater than 20.

In various embodiments, reporter 1610 may be any one selected from a group including a volatile organic compound, an elemental mass tag, a peptide comprising one or more D-amino acids, a nucleic acid, and a neoantigen. In one embodiment, reporter 1610 includes an antigen detectable by a hybridization assay. The method of detection may be selected based on the type of reporter 1610 used. For example, a volatile organic compound may be detected via a gas chromatography instrument, a breathalyzer, a mass spectrometer, or use of optical or acoustic sensors.

Figure 17:
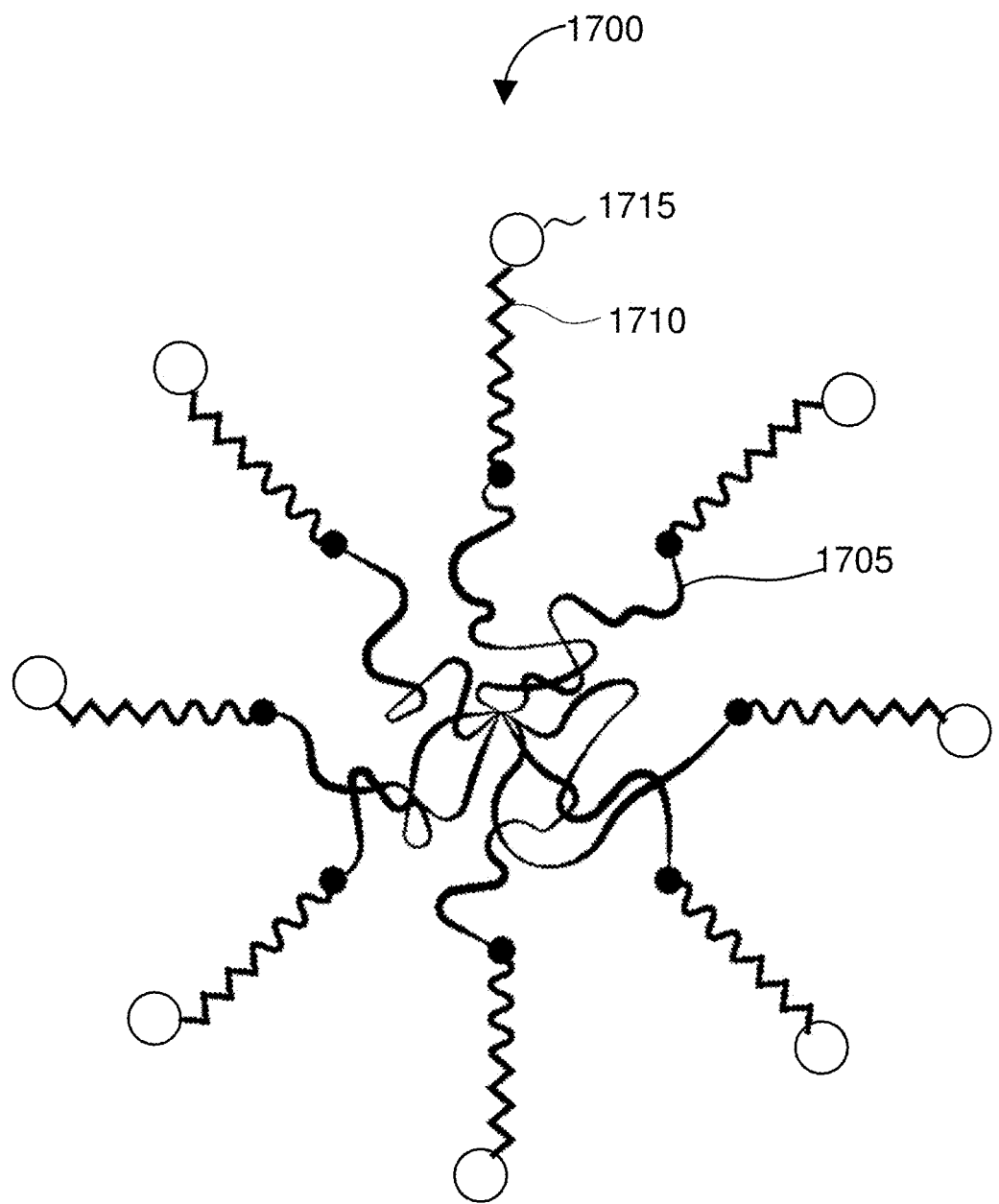
FIG. 17 shows an activity sensor with a detectable analyte formed by tuning domains.

FIG. 17 shows an activity sensor 1700 with polypeptide reporters 1710 that release a detectable analyte when released from polypeptides 1710, and tuning domains 1715 that form a portion of the detectable analyte.

When administered to a subject, the activity sensor 1700 is trafficked in the body through various pathways depending on how it enters the body. For example, if the activity sensor 1700 is administered intravenously, it will enter systemic circulation from the point of injection and may be passively trafficked through the body.

For activity sensor 1700 to detect an enzymatic activity within a specific cell, at some point during its residence time in the body, the activity sensor must come into the presence of the enzyme and have an opportunity for reporters 1710 to be cleaved by the target enzyme. Enzymes can distinguish between very similar substrate molecules because enzymes are chemoselective (i.e., preferring an outcome of a chemical reaction over an alternative reaction), regioselective (i.e., preferring one direction of chemical bond making or breaking over all other possible directions), and stereospecific (i.e., only reacting on one or a subset of stereoisomers). Amino acids may occur as either L- or D-amino acids. L- and D-amino acids generally refer to the left-handed and right-handed configurations of an amino acid, respectively, and represent two different enantiomers (stereoisomers) around the central carbon atom.

Generally, only L-amino acids are manufactured in cells; D-amino acids are not. Because enzymes are stereospecific, peptides composed of D-amino acids are resistant to endogenous peptidases and proteases, and are less likely to induce humoral immune responses in a subject.

In one embodiment, by providing tuning domains 1715 that form a portion of the detectable analyte, where tuning domains 1715 include D-amino acids, the D-amino acids may prevent further proteolytic cleavage of the detectable analyte after it is released from polypeptide 1710.

Activity sensor 1700 includes a bio-compatible scaffold carrier 1705 and polypeptide reporters 1710 linked to scaffold 1705, and tuning domains 1715 that form a portion of the detectable analyte released from polypeptides 1710 when polypeptides 1710 are cleaved.

As illustrated, an 8-arm PEG-MAL scaffold 1705 is provided as the carrier, where the terminal end of each arm is linked to a polypeptide reporter 1710. Polypeptides 1715 are linked to polypeptide reporters 1710, thereby forming a portion of the detectable analyte. When proteases cleave polypeptides 1710, a detectable analyte is released, which includes polypeptide tuning domains 1715. As shown, tuning domains 1715 include D-amino acids that form a portion of the detectable analyte.

One of skill in the art would know what peptide segments to include as protease cleave sites in an activity sensor of the disclosure. One can use an online tool or publication to identify cleave sites. For example, cleave sites are predicted in the online database PROSPER, described in Song, 2012, PROSPER: An integrated feature-based tool for predicting protease substrate cleavage sites, PLoS One 7(11):e50300, incorporated by reference. Reproduced below is a set of exemplary protease substrates for a variety of significant protease. In the sequences shown below, the vertical bar shows the cleavage site, and forms no part of the sequence. Any of the compositions, structures, methods or activity sensors discussed herein may include, for example, any suitable cleavage site such as the sequences below as cleavage sites, as well as any further arbitrary polypeptide segment to obtain any desired molecular weight. To prevent off-target cleavage, one or any number of amino acids outside of the cleavage site may be in a mixture of the D and/or the L form in any quantity.

```
Aspartic protease HIV-1 retropepsin (A02.001)
A02.001:
                                            (SEQ ID NO: 1)
SSTS|SWYS

A02.001:
                                            (SEQ ID NO: 2)
PCIQ|AESE

A02.001:
                                            (SEQ ID NO: 3)
DDEE|IELA

A02.001:
                                            (SEQ ID NO: 4)
VLEQ|VVTS

A02.001:
                                            (SEQ ID NO: 5)
QVVQ|VVLD

Cysteine protease Cathepsin K (C01.036)
C01.036:
                                            (SEQ ID NO: 6)
KSIQ|EIQE
```

C01.036:
KDFA|AEVV (SEQ ID NO: 7)

C01.036:
TSYA|GYIE (SEQ ID NO: 8)

C01.036:
LKVA|GQDG (SEQ ID NO: 9)

C01.036:
FCLH|GGLS (SEQ ID NO: 10)

Calpain-1 (C02.001)
C02.001:
WMDF|GRRS (SEQ ID NO: 11)

C02.001:
SATA|AVNP (SEQ ID NO: 12)

C02.001:
RELG|LGRH (SEQ ID NO: 13)

Caspase-1 (C14.001)
C14.004:
DEGD|SLDG (SEQ ID NO: 14)

C14.004:
DETD|MAKL (SEQ ID NO: 15)

C14.004:
EECD|AAEG (SEQ ID NO: 16)

Caspase-3 (C14.003)
C14.003:
AEVD|GDDD (SEQ ID NO: 17)

C14.003:
DRHD|GTSN (SEQ ID NO: 18)

C14.003:
VEVD|APKS (SEQ ID NO: 19)

Caspase-7 (C14.004)
C14.004:
DQTD|GLGL (SEQ ID NO: 20)

C14.004:
DSID|SFET (SEQ ID NO: 21)

C14.004:
DDVD|TKKQ (SEQ ID NO: 22)

Caspase-6 (C14.005)
C14.005:
VEMD|AAPG (SEQ ID NO: 23)

C14.005:
VSWD|SGGS (SEQ ID NO: 24)

C14.005:
EETD|GIAY (SEQ ID NO: 25)

Caspase-8 (C14.009)
C14.003:
VETD|KATV (SEQ ID NO: 26)

C14.003:
GSSD|PLIQ (SEQ ID NO: 27)

C14.003:
DDAD|YKPK (SEQ ID NO: 28)

Metalloprotease Matrix metallopeptidase-2 (M10.003)
M10.003:
HISS|LIKL (SEQ ID NO: 29)

M10.003:
DPNN|LLND (SEQ ID NO: 30)

M10.003:
DLSD|LTAA (SEQ ID NO: 31)

M10.003:
FSAY|IKNS (SEQ ID NO: 32)

M10.003:
EALP|LLVR (SEQ ID NO: 33)

Matrix metallopeptidase-9 (M10.004)
M10.004:
QQGA|IGSP (SEQ ID NO: 34)

M10.004:
GPPG|IVIG (SEQ ID NO: 35)

M10.004:
MDIA|IHHP (SEQ ID NO: 36)

M10.004:
FFKN|IVTP (SEQ ID NO: 37)

M10.004:
GPLG|ARGI (SEQ ID NO: 38)

Matrix metallopeptidase-3 (M10.005)
M10.005:
HLGG|AKQV (SEQ ID NO: 39)

M10.005:
VWAA|EAIS (SEQ ID NO: 40)

M10.005:
GPLG|ARGI (SEQ ID NO: 41)

M10.005:
ESGD|YKAT (SEQ ID NO: 42)

Matrix metallopeptidase-7 (M10.008)
M10.008:
VAQD|LNAP (SEQ ID NO: 43)

-continued

M10.008:

SPDA|LQNP (SEQ ID NO: 44)

M10.008:

PPLK|LMHS (SEQ ID NO: 45)

M10.008:

GPHL|LVEA (SEQ ID NO: 46)

Serine protease Chymotrypsin A (cattle-type) (S01.001)
S01.001:

VGPN|LHGV (SEQ ID NO: 47)

S01.001:

GGGN|KIGP (SEQ ID NO: 48)

Granzyme B (Homo sapiens-type) (S01.010)
S26.010:

LSTA|RFVV (SEQ ID NO: 49)

S26.010:

VTED|VDIN (SEQ ID NO: 50)

S26.010:

SALA|TTVY (SEQ ID NO: 51)

Elastase-2 (S01.131)
S01.131:

QELI|SNAS (SEQ ID NO: 52)

S01.131:

QELI|SNAS (SEQ ID NO: 53)

S01.131:

WELI|SNAS (SEQ ID NO: 54)

Cathepsin G (S01.133)
S01.133:

SGNY|ATVI (SEQ ID NO: 55)

S01.133:

SIQM|NVAE (SEQ ID NO: 56)

S01.133:

QQNY|QNSE (SEQ ID NO: 57)

Thrombin (S01.217)
S01.217:

SILR|LAKA (SEQ ID NO: 58)

S01.217:

KFQR|AITG (SEQ ID NO: 59)

S01.217:

AEPK|MHKT (SEQ ID NO: 60)

S01.217:

TIPR|AAIN (SEQ ID NO: 61)

-continued

Plasmin (S01.233)
S01.233:

AEFR|HDSG (SEQ ID NO: 62)

S01.233:

RRKR|IVGG (SEQ ID NO: 63)

S01.233:

AMSR|MSLS (SEQ ID NO: 64)

Glutamyl peptidase I (S01.269)
S01.269:

PEPE|QLKM (SEQ ID NO: 65)

S01.269:

QSKE|AIHS (SEQ ID NO: 66)

S01.269:

KLKE|ASRS (SEQ ID NO: 67)

Furin (S08.071)
S08.071:

RAKR|SPKH (SEQ ID NO: 68)

S08.071:

RKKR|STSA (SEQ ID NO: 69)

Signal peptidase I (S26.001)
S26.001:

SAMA|ADSN (SEQ ID NO: 70)

S26.001:

TLLA|NINE (SEQ ID NO: 71)

Thylakoidal processing peptidase (S26.008)
S01.269:

QAEE|TYEN (SEQ ID NO: 72)

S01.269:

DVID|MSKE (SEQ ID NO: 73)

Signalase (animal) 21 KDa component (S26.010)
S26.010:

EVLA|TPPA (SEQ ID NO: 74)

S26.010:

APVP|GTAW (SEQ ID NO: 75)

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein.

EXAMPLES

Tuning an Activity Sensor to Detect Liver Fibrosis

Liver fibrosis is a wound healing response to chronic liver injury and results in the formation of scar tissue that can lead to cirrhosis, liver failure and cancer. As liver fibrosis develops, the extracellular matrix of liver tissue is rearranged, primarily due to dysregulated protease activity, for example, matrix remodeling proteases such as matrix metalloproteinases (MMPs) and their inhibitors.

To diagnose enzymatic activity indicative of liver fibrosis, gene expression in subjects known to have liver fibrosis may be determined, proteases expressed in the subjects having liver fibrosis are identified, and an activity sensor may be assembled. The activity sensor may then be administered to a subject having liver fibrosis to diagnose the disease based on detection of protease activity on substrates known to be cleaved by the proteases expressed by cells with liver fibrosis. The activity sensor includes a carrier, at least one tuning domain that modifies a distribution or residence time of the activity sensor within a subject when administered to the subject, and at least one reporter linked to the carrier, in which the reporter includes substrates for the proteases identified.

When administered to a subject with liver fibrosis, the activity sensor is trafficked to liver via the body's circulation and enters the disease microenvironment through organ- or disease-specific vascular fenestrations, for example, the liver sinusoid epithelium, a sinusoidal blood vessel with fenestrated due to a discontinuous endothelium that serves as a location for mixing of the oxygen-rich blood from the hepatic artery and the nutrient-rich blood from the portal vein.

In the disease microenvironment, such as the liver, the reporter may be cleaved from the carrier by proteases specific to the selected substrate incorporated into the reporter. When liberated from the carrier, the reporter re-enters circulation, passes renal filtration, and is excreted from the subject where it may be detected, thereby detecting the target protease activity.

Determining Gene Expression

To determine gene expression in subjects known to have liver fibrosis, a list of candidate peptide substrates may be assembled from research discussing proteases active or dysregulated during the progression of liver fibrosis. The list of peptide substrates of the proteases implicated in liver fibrosis were identified as candidate substrates.

Identify Proteases Expressed in the Subjects having Liver Fibrosis

Fluorescein-labeled derivatives of ~50 candidate peptide substrates were conjugated to PEG-coated, long-circulating iron oxide nanoworm (NW) activity sensors and incubated with recombinant proteases commonly overexpressed in liver fibrosis, for example, MMPs and cathepsins. Relative substrate activities for each protease-substrate combination were determined by monitoring increases in sample fluorescence resulting from peptidolysis, allowing previously homoquenched fluorophores to freely emit in solution. By assessing relative florescence of each substrate activity, a library of peptide substrates with broad protease susceptibility were selected.

Assembling the Activity Sensor

After identifying proteases expressed in subjects having liver fibrosis and selecting peptide substrates susceptible to the identified proteases, an activity sensor that may be used to detect the protease activity was assembled. The activity sensor includes a carrier, at least one tuning domain that modifies a distribution or residence time of the activity sensor within a subject when administered to the subject. The reporter is constructed as a polypeptide incorporating the identified protease substrate. The carrier is chosen to be a biocompatible scaffold containing multiple subunits of covalently linked poly(ethylene glycol) maleimide, an 8-arm PEG-MAL scaffold. Each of the reporter peptide chains are conjugated to each of the eight arms of the carrier via maleimide-thiol coupling. PEG tuning domains are linked to each of the activity sensors to shield the polypeptides from immune detection or inhibit cellular uptake of the activity sensor by macrophages because, when administered to a subject with liver fibrosis, the activity sensor must be trafficked to the liver to detect dysregulated protease activity in the liver.

By providing the activity sensor with the PEG tuning domains, the distribution and residence time of the activity sensor is improved relative to an activity sensor lacking the tuning domains. As such, the activity sensor will be trafficked to the liver through the circulatory system when administered intravenously, while the tuning domains prevent immune detection and clearance by white blood cells and inhibit cellular uptake by macrophages present in circulation and in tissues of the liver.

Upon reaching the liver, the activity sensor enters the diseased microenvironment and the protease susceptible substrate of the reporter is cleaved by proteases present in the diseased area, liberating the reporter from the carrier. The liberated reporter then re-enters circulation where it passes renal filtration and is excreted in urine. A urine sample is obtained from the subject having liver fibrosis and the reporter is detected, for example, by mass spectrometry, thereby detecting the target protease activity associated with a state of liver fibrosis, or the progression or regression of liver fibrosis in the subject.

What is claimed is:

1. An activity sensor comprising:
a carrier comprising a polyethylene glycol (PEG) scaffold comprised of covalently linked PEG subunits; and
at least two distinct detectable peptide reporters, wherein each of said at least two distinct detectable peptide reporters is linked to the carrier by a cleavable peptide linker containing a cleavage site for one of at least two different enzymes, wherein the activity sensor reports differential enzyme activity among the at least two different enzymes by releasing the detectable peptide reporters upon cleavage of the cleavable peptide linker by the at least two different enzymes;
wherein each of the detectable peptide reporters is coupled to a biocompatible polymer,
wherein the biocompatible polymer is configured to stabilize and protect each of the coupled detectable peptide reporters from immune detection before and after cleavage of the cleavable peptide linker.

2. The activity sensor of claim 1, wherein at least four detectable peptide reporters are linked via cleavage sites to report activity of at least four different enzymes.

3. The activity sensor of claim 1, wherein the cleavable peptide linker comprises a polypeptide susceptible to cleavage by a protease.

4. The activity sensor of claim 1, wherein the PEG scaffold comprises a multi-arm PEG scaffold.

5. The activity sensor of claim 1, wherein:
the PEG scaffold is 30 to 40 kDa.

6. The activity sensor of claim 1, wherein the cleavable peptide linker is configured to be cleaved by proteases associated with a disease or physiological state and the biocompatible polymer facilitates passage of the detectable peptide reporters into systemic circulation after cleavage.

7. The activity sensor of claim 1, wherein the biocompatible polymer is configured to inhibit enzymatic activity upon the liberated detectable peptide reporters prior to excretion from a subject.

8. The activity sensor of claim 1, wherein the cleavable peptide linker is susceptible to cleavage by a protease to release a detectable analyte, and wherein each detectable peptide reporters comprises the detectable analyte.

9. The activity sensor of claim 6, wherein the disease or physiological state is associated with liver fibrosis.

10. The activity sensor of claim 6, wherein the disease or physiological state is associated with nonalcoholic fatty liver disease (NAFLD).

11. The activity sensor of claim 7, wherein excretion from the subject comprises excretion in urine.

12. The activity sensor of claim 1, wherein the immune detection before cleavage of the cleavable peptide linker comprises immune detection by white blood cells and cellular uptake by macrophages present in circulation and in tissues of a liver of a subject.

* * * * *